US011402367B2

(12) United States Patent
Maoz et al.

(10) Patent No.: US 11,402,367 B2
(45) Date of Patent: Aug. 2, 2022

(54) INTEGRATED MULTI-ELECTRODE ARRAY AND TRANS-ENDOTHELIAL ELECTRICAL RESISTANCE IN ORGAN-ON-A-CHIP MICROSYSTEMS

(71) Applicant: President and Fellows of Harvard College, Cambridge, MA (US)

(72) Inventors: Ben M. Maoz, Tel Aviv (IL); Anna Herland, Linkoping (SE); Olivier F. Henry, Brookline, MA (US); Kevin K. Parker, Cambridge, MA (US); Donald E. Ingber, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 143 days.

(21) Appl. No.: 16/488,754

(22) PCT Filed: Feb. 26, 2018

(86) PCT No.: PCT/US2018/019754
§ 371 (c)(1),
(2) Date: Aug. 26, 2019

(87) PCT Pub. No.: WO2018/157073
PCT Pub. Date: Aug. 20, 2018

(65) Prior Publication Data
US 2020/0049689 A1  Feb. 13, 2020

Related U.S. Application Data

(60) Provisional application No. 62/506,420, filed on May 15, 2017, provisional application No. 62/464,229, filed on Feb. 27, 2017.

(51) Int. Cl.
*G01N 33/483* (2006.01)
*B01L 3/00* (2006.01)
(Continued)

(52) U.S. Cl.
CPC ........ *G01N 33/4836* (2013.01); *B01L 3/5027* (2013.01); *C12M 23/16* (2013.01);
(Continued)

(58) Field of Classification Search
CPC ..... B01L 3/5207; C12M 23/16; C12M 25/02; C12M 41/46; C12M 35/08; G01N 33/4836; G01N 33/48728
See application file for complete search history.

(56) References Cited

U.S. PATENT DOCUMENTS 6,312,952 B1 * 11/2001 Hicks, Jr. ............ C12N 5/0068
435/177
2012/0211373 A1 * 8/2012 El-Sayed ............... C12M 35/02
205/778
(Continued)

OTHER PUBLICATIONS

Tang et al. "Fabrication of strongly adherent black coatings on microelectrode arrays" (Sci China Inf Sci, 2014, 57: 042402:1-042402:10). (Year: 2014).*
(Continued)

*Primary Examiner* — Michael L Hobbs
(74) *Attorney, Agent, or Firm* — Nixon Peabody LLP

(57) ABSTRACT

An organ-on-chip device for monitoring a biological function and including a membrane layer located at an interface region between a top microchannel and the a microchannel. The membrane includes a first type of cells forming a barrier between the top microchannel and the bottom microchannel. The device further includes a top layer having a first plurality of transendothelial electrical resistance (TEER) measurement electrodes for enabling direct monitoring of cell function and electrical activity of the first type of cells on the membrane. The device also has a multi-electrode array (MEA) layer with a second plurality of TEER measurement electrodes for enabling direct monitoring of cell
(Continued)

function and electrical activity of a second type of cells on the MEA layer.

4 Claims, 13 Drawing Sheets

(51) Int. Cl.
    *C12M 3/06*     (2006.01)
    *C12M 1/12*     (2006.01)
    *C12M 1/34*     (2006.01)
    *G01N 33/487*     (2006.01)

(52) U.S. Cl.
    CPC ............ *C12M 25/02* (2013.01); *C12M 41/46* (2013.01); *G01N 33/48728* (2013.01)

(56) References Cited

U.S. PATENT DOCUMENTS

| | | | |
|---|---|---|---|
| 2014/0342445 A1 | 11/2014 | Ingber | |
| 2018/0372711 A1* | 12/2018 | Rajasekaran | B01L 3/502715 |
| 2019/0025240 A1* | 1/2019 | Henry | C12M 41/46 |

OTHER PUBLICATIONS

International Search Report and Written Opinion in International Patent Application No. PCT/US2018/019754, dated Jul. 16, 2018 (12 pages).
Williams, S.; "Master's Thesis: Fabrication of a Microfluidic Platform for Impedance Analysis of Cultured Endothelial Cell Monolayers"; *Electronic Theses and Dissertations*; Paper 1577; University of Louisville, Dec. 2005, retrieved from https://ir.library.louisville.edu/cgi/viewcontent.cgi?article=2576&content=etd, on Apr. 19, 2018 (169 pages).
Esch, E. W. et al.; "Organs-on-chips at the frontiers of drug discovery"; *Nat. Rev. Drug Discov.* vol. 14, 248-260; Apr. 2015 (13 pages).
Wu, M.-H. et al.; "Microfluidic cell culture systems for drug research"; *Lab Chip*, vol. 10, pp. 939-956; Jan. 21, 2010 (18 pages).
Capulli, A. K. et al.; "Approaching the in vitro clinical trial: engineering organs on chips"; *Lab Chip* 14, pp. 3181-3186 (2014) (7 pages).
Bhatia, S. N. et al.; "Microfluidic organs-on-chips"; *Nat. Biotechnol.* vol. 32, No. 8, pp. 760-772; Aug. 2014 (2 pages).
Ingber, D. E.; "Reverse Engineering Human Pathophysiology with Organs-on-Chips"; *Cell* 164, pp. 1105-1109; Mar. 10, 2016 (5 pages).
Bavli, D. et al.; "Real-time monitoring of metabolic function in liver-on-chip microdevices tracks the dynamics of mitochondrial dysfunction"; *Proc. Natl. Acad. Sci. U. S. A.* E2231-2240 (Apr. 4, 2016). doi:10.1073/pnas.1522556113 (10 pages).
El-Ali, J. et al.; "Cells on chips"; *Nature*, vol. 442, pp. 403-411; Jul. 27, 2006 (9 pages).
Visone, R. et al.; "Cardiac Meets Skeletal: What's New in Microfluidic Models for Muscle Tissue Engineering"; *Molecules* 21, 1-21; Aug. 26, 2016 (21 pages).
Srinivasan, B. et al.; TEER measurement techniques for in vitro barrier model systems. *J Lab Autom.* 20, pp. 107-126; Apr. 2015 (35 pages).
Griep, L. M. et al.; BBB on CHIP: Microfluidic platform to mechanically and biochemically modulate blood-brain barrier function; *Biomed. Microdevices* 15, pp. 145-150 (2013) (6 pages).
Booth, R. et al.; "Characterization of a microfluidic in vitro model of the blood-brain barrier (µBBB)"; *Lab Chip* vol. 12, No. 10, pp. 1784-1792 (2012) (10 pages).
Kim, H. J. et al.; Contributions of microbiome and mechanical deformation to intestinal bacterial overgrowth and inflammation in a human gut-on-a-chip; *Proc. Natl. Acad. Sci.* 113, pp. E7-E15; Dec. 14, 2015 (9 pages)

Huh, D. et al.; "Reconstituting organ-level lung functions on a chip", *Science* vol. 328, pp. 1662-1668; Jun. 25, 2010 (8 pages).
Walter, F. R. et al.; "A versatile lab-on-a-chip tool for modeling biological barriers"; *Sensors Actuators, B Chem.* 222, pp. 1209-1219 (2016) (4 pages).
Odijk, M. et al.; "Measuring direct current trans-epithelial electrical resistance in organ-on-a-chip microsystems"; *Lab Chip* 15, pp. 745-752 (2015) (8 pages).
Van der Helm, M. W. et al.; Microfluidic organ-on-chip technology for blood-brain barrier research; *Tissue Barriers*, vol. 4, Issue 1, e1142493-1 (2016) (13 pages).
Spira, M. E. et al.; "Multi-electrode array technologies for neuroscience and cardiology"; *Nat. Nanotechnol.* vol. 8, pp. 83-94; Feb. 5, 2013 (12 pages).
Taketani, M. et al.; *Advances in Network Electrophysiology Using Multi-Elecrode Arrays*. (2006) (488 pages).
Caspi, O. et al.; "In vitro electrophysiological drug testing using human embryonic stem cell derived cardiomyocytes"; *Stem Cells Dev.*, vol. 18, No. 1, pp. 161-172 (2009); (15 pages).
Lahti, A. L. et al.; "Model for long QT syndrome type 2 using human iPS cells demonstrates arrhythmogenic characteristics in cell culture"; *Dis. Model. Mech.*, vol. 5, No. 2, pp. 220-230; Mar. 2012 (23 pages).
Kujala, V. et al.; "Laminar Ventricular Myocardium on a Microelectrode Array-Based Chip"; *J. Mater. Chem. B*, vol. 4, pp. 3534-3543 (2016) (10 pages).
Doña Rodríguez, J. M. et al.; "Determination of the Real Surface Area of Pt Electrodes by Hydrogen Adsorption Using Cyclic Voltamrnetry"; *J. Chem. Educ.*, vol. 77, No. 9, pp. 1195-1197; Sep. 2000 (3 pages).
Tang, L. et al.; "A facile route for irreversible bonding of plastic-PDMS hybrid microdevices at room temperature"; *Lab Chip*, vol. 10, pp. 1274-1280; Feb. 16, 2010 (7 pages).
Lee, N. Y. et al.; "Novel Poly(dimethylsiloxane) Bonding Strategy Via Room Temperature 'Chemical Gluing'"; *Langmuir* 25, pp. 3861-3866; Feb. 17, 2009 (6 pages).
Lee, K. S. et al.; "Plastic-PDMS bonding for high pressure hydrolytically stable active microfluidics"; *Lab Chip*, vol. 9, pp. 1618-1624; Mar. 13, 2009 (7 pages).
Watson, S. et al.; "Challenges and developments of self-assembled monolayers and polymer brushes as a green lubrication solution for tribological applications"; *RSC Adv.* 5, pp. 89698-89730 (2015) (33 pages).
Li, C. et al.; "The Mechanism for 3-Aminopropyltriethoxysilane to Strengthen the Interface of Polycarbonate Substrates with Hybrid Organic-Inorganic Sol-Gel Coatings"; *J. Inorg. Organomet. Polym.* vol. 7, No. 4, pp. 203-216 (1997) (14 pages).
Fadeev, A. Y. et al.; "Surface Modification of Poly(ethylene terephthalate) To Prepare Surfaces with Silica-Like Reactivity"; *Langmuir*, vol. 14, pp. 5586-5593 (Aug. 21, 1998) (8 pages).
Son, Y.; Determination of shear viscosity and shear rate from pressure drop and flow rate relationship in a rectangular channel; *Polymer (Guildf).*, vol. 48, No. 2, pp. 632-637 (2007) (7 pages).
Heer, F. et al.; "CMOS microelectrode array for the monitoring of electrogenic cells"; *Biosens. Bioelectron.*, 20, pp. 358-366; Mar. 19, 2004 (9 pages).
Moghadarn, F. H. et al.; "Transplantation of primed or unprimed mouse embryonic stem cell-derived neural precursor cells improves cognitive function in Alzheimerian rats"; *Differentiation.*, vol. 78, pp. 59-68; Jun. 25, 2009 (10 pages).
Lind, J. U. et al.; "Instrumented cardiac microphysiological devices via multimaterial three-dimensional printing"; *Nat. Mater.* vol. 16, p. 303; doi:10.103; Oct. 24, 2016 (1 page).
Förster, C. et al.; "Differential effects of hydrocortisone and TNFalpha on tight junction proteins in an in vitro model of the human blood-brain barrier"; *J. Physiol.*, 586.7 , pp. 1937-1949 (Feb. 7, 2008) (13 pages).
Dewi, B. E. et al.; "In vitro assessment of human endothelial cell permeability: Effects of inflammatory cytokines and dengue virus infection"; *J. Virol. Methods*, vol. 121, pp. 171-180; Aug. 6, 2004 (10 pages).
Opp, D. et al.; "Use of electric cell-substrate impedance sensing to assess in vitro cytotoxicity"; *Biosens. Bioelectron.*, vol. 24, pp. 2625-2629; Jan. 23, 2009 (5 pages).

(56) References Cited

OTHER PUBLICATIONS

Michaelis, S. et al.; "Studying Cell-Surface Interactions in Vitro: A Survey of Experimental Approaches and Techniques"; in *Tissue Engineering III: Cell-Surface Interactions for Tissue Culture*; pp. 33-66 (2012). (48 pages).

Lee, R. et al., "Real-time and label-free monitoring of nanoparticle cellular uptake using capacitance-based assays"; *Sci. Rep.* 6, 33668; doi: 10.1038/srep33668; Sep. 19, 2016 (10 pages).

Feldman, A. M. et al.; "The Role of Tumor Necrosis Factor in the Pathophysiology of Heart Failure"; *J Am Coll. Cardiol.*, vol. 35, No. 3, pp. 537-544; Mar. 1, 2000 (8 pages).

\* cited by examiner

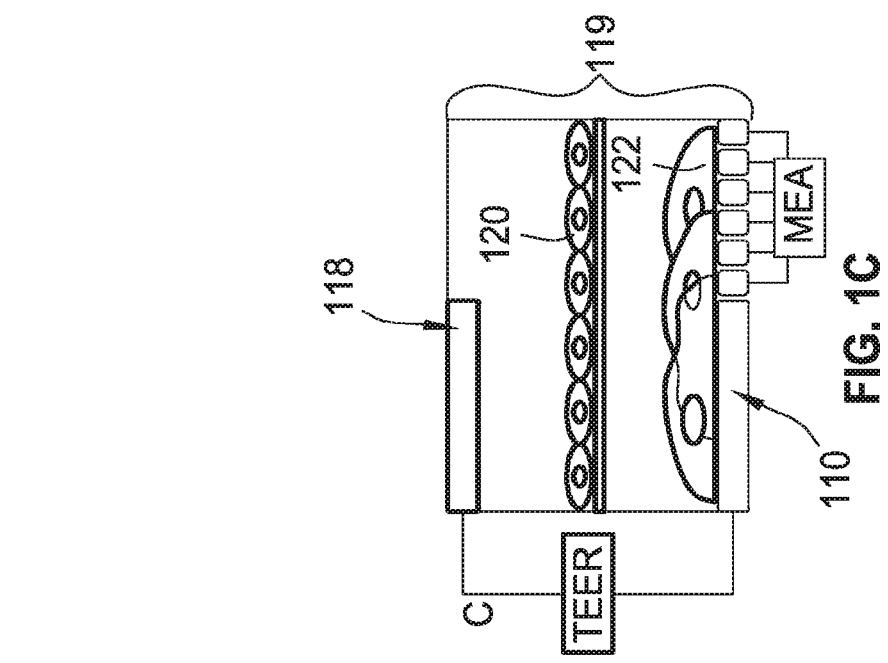
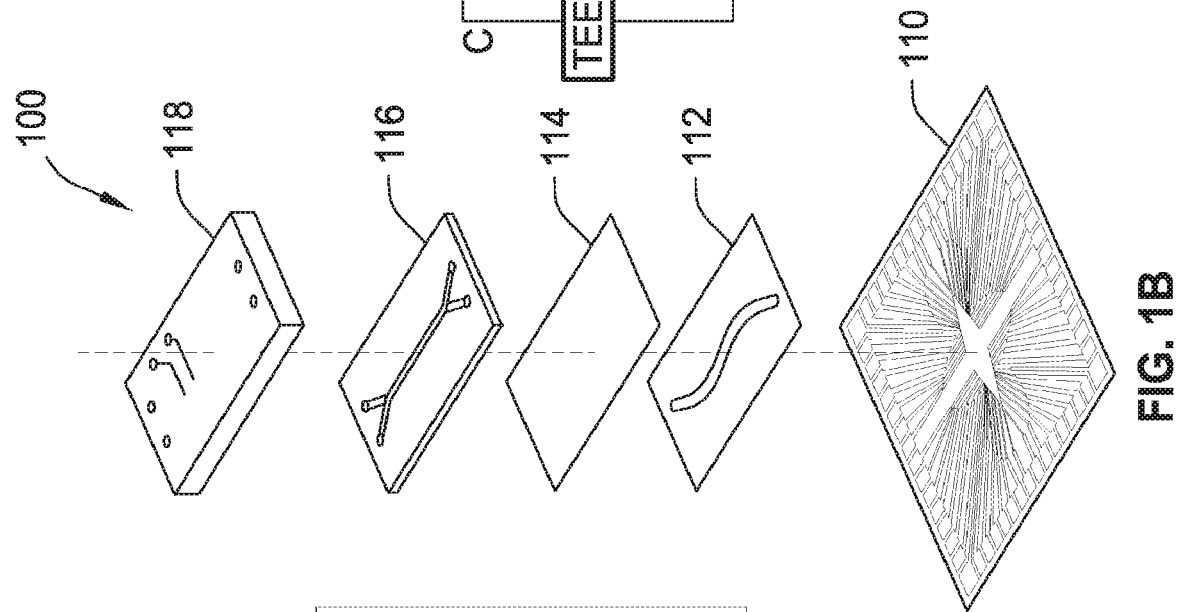
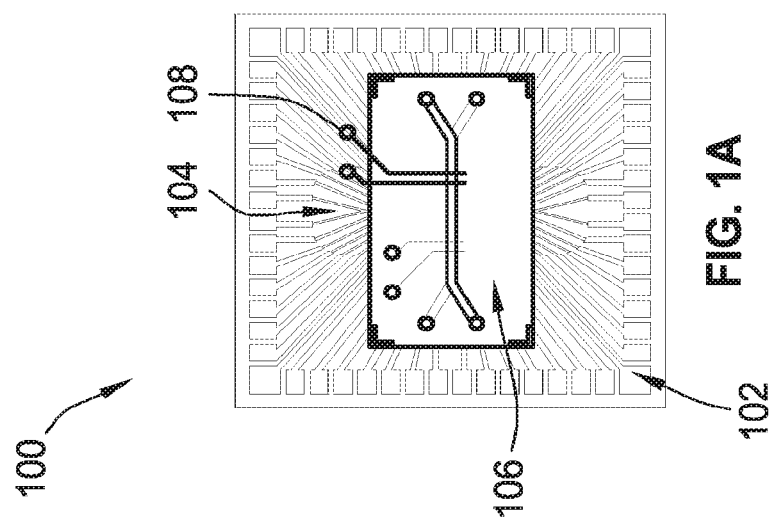
FIG. 1A
FIG. 1B
FIG. 1C

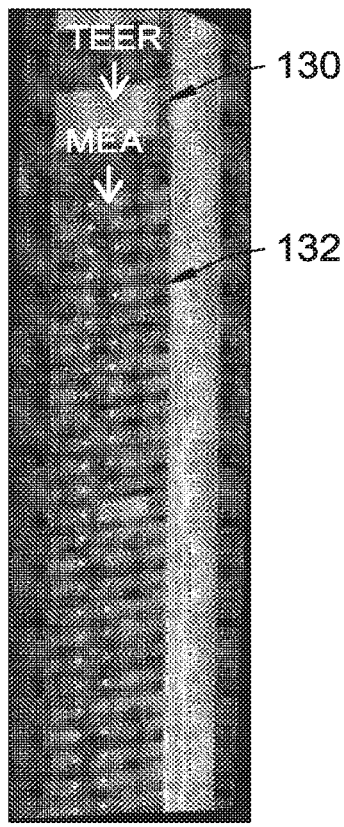
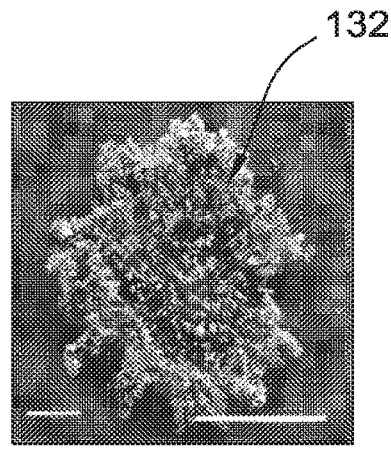
FIG. 2A
FIG. 2B
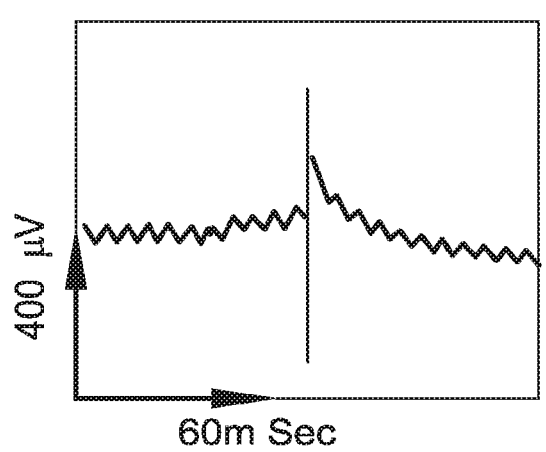
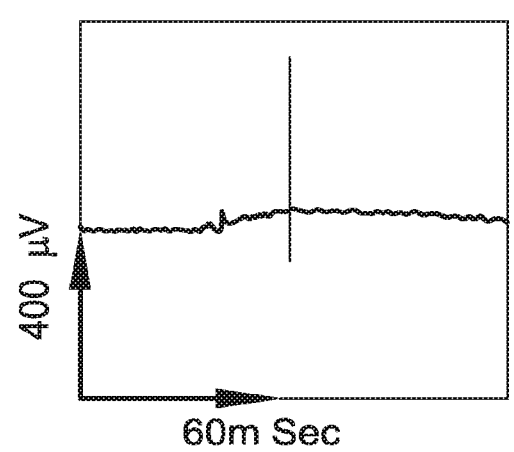
FIG. 2C
FIG. 2D

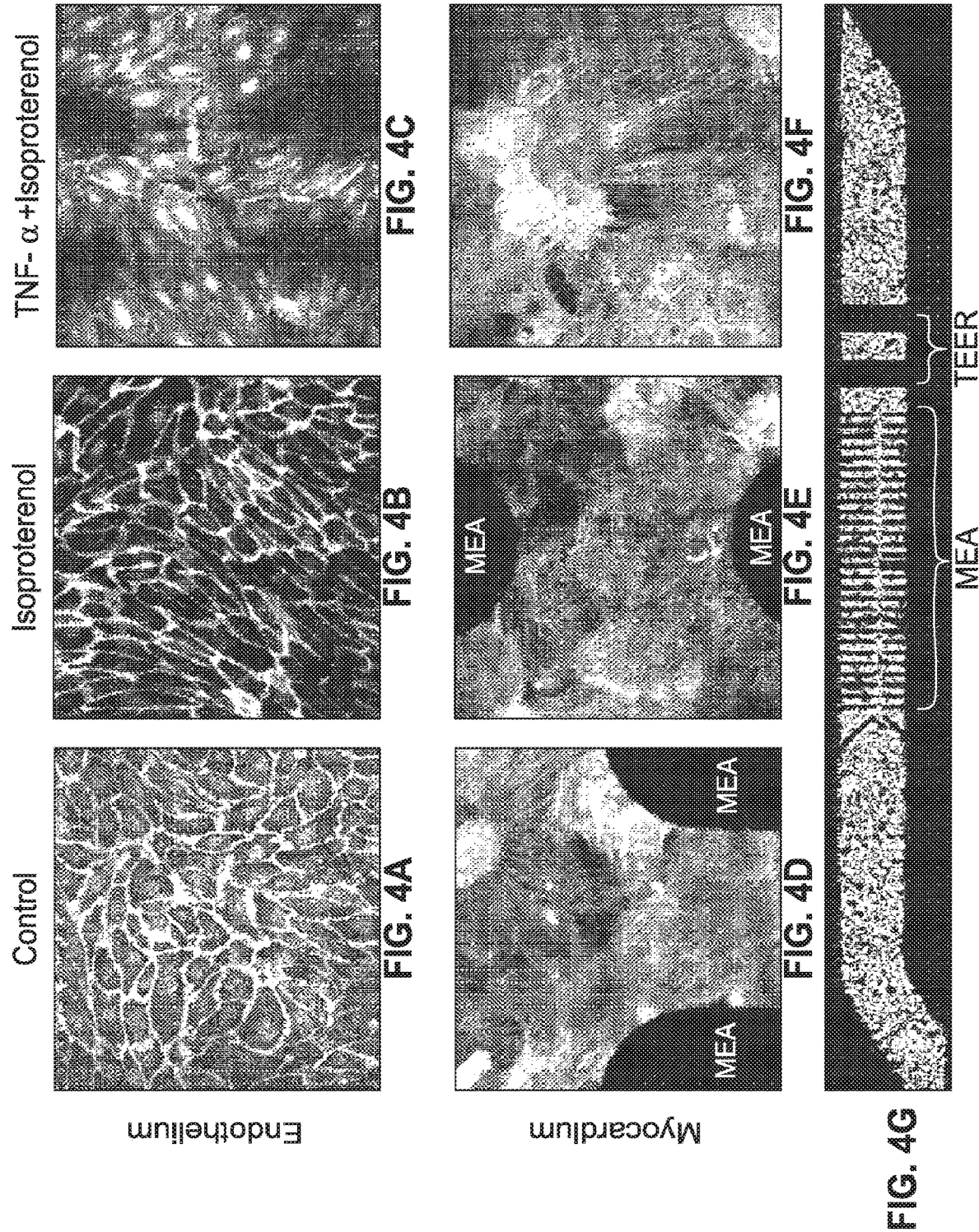

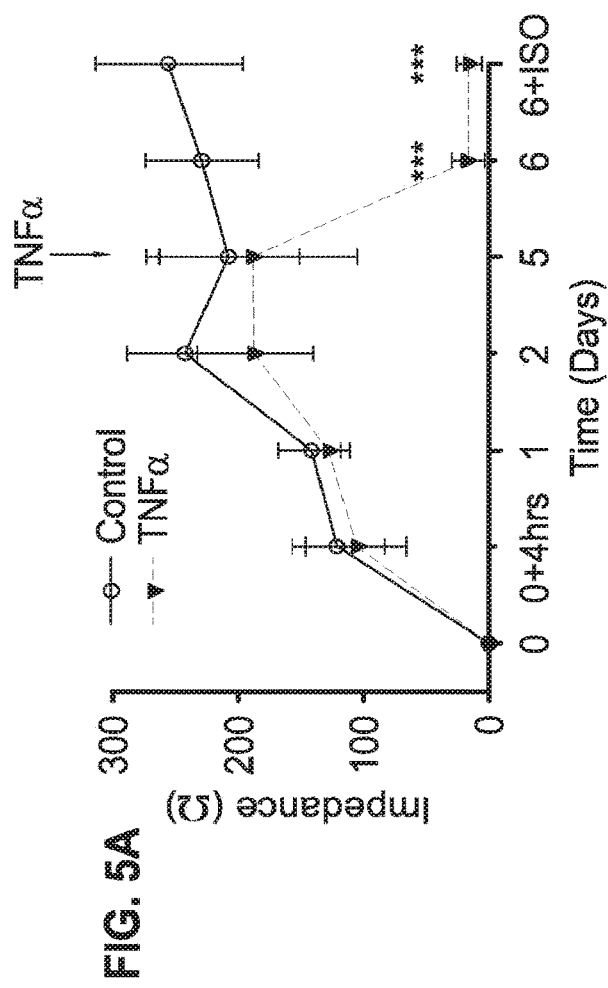
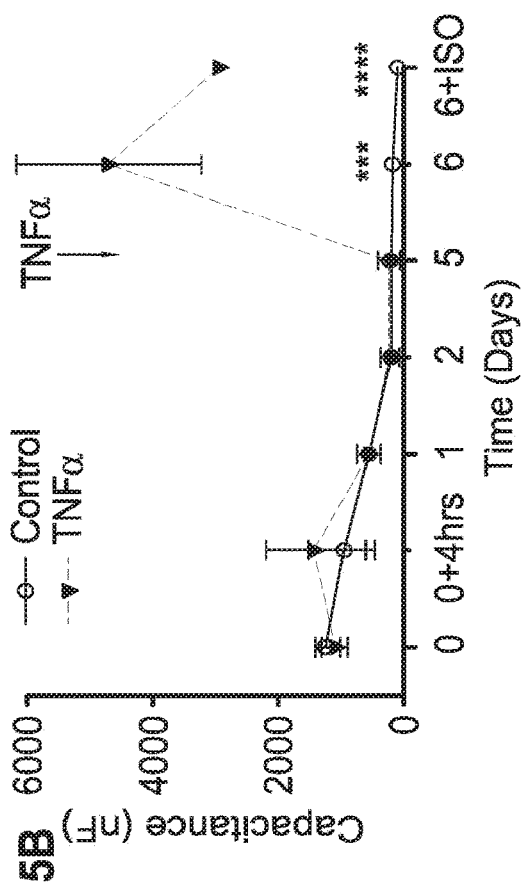
FIG. 5A
FIG. 5B
FIG. 5C
FIG. 5D

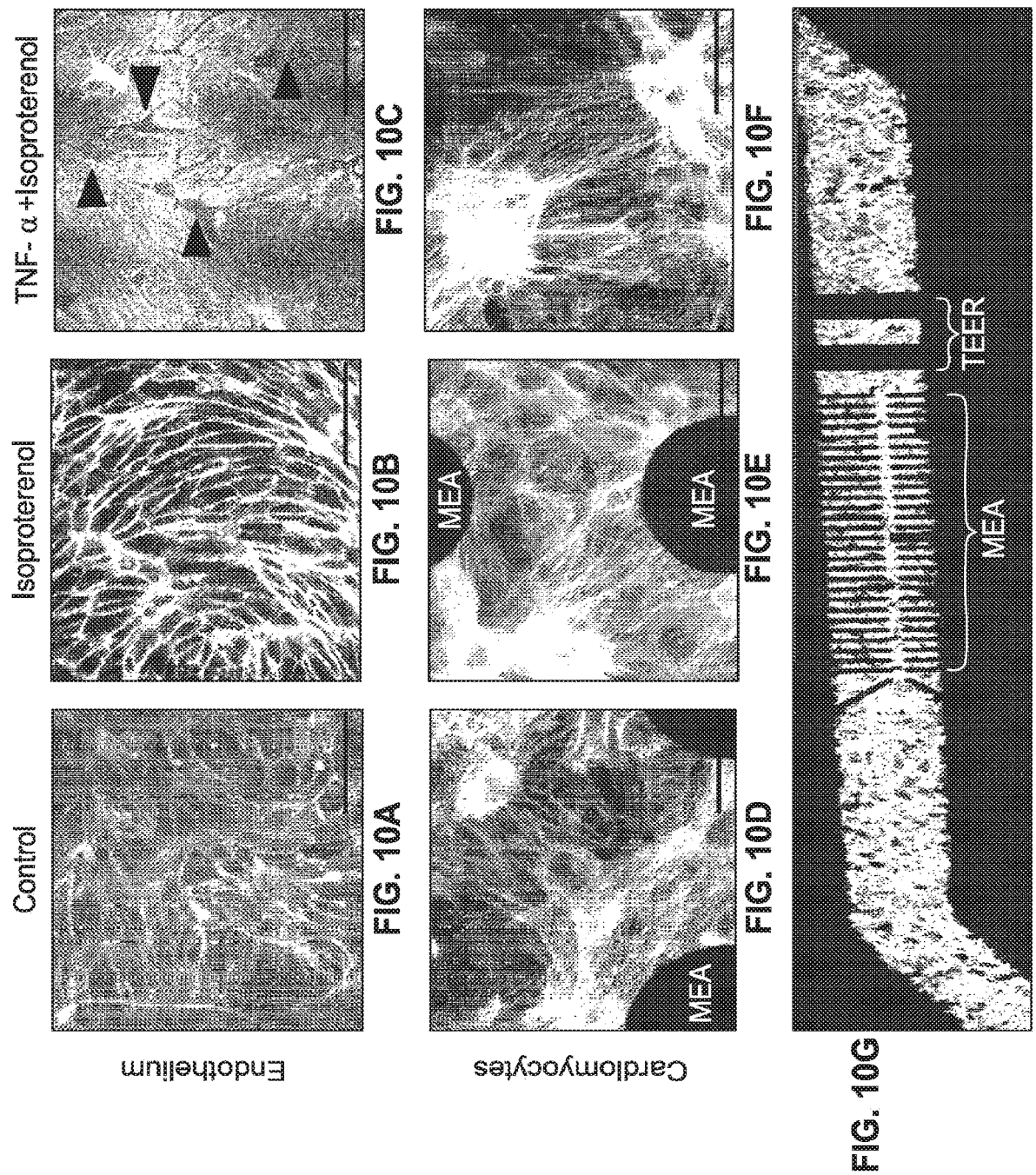

INTEGRATED MULTI-ELECTRODE ARRAY AND TRANS-ENDOTHELIAL ELECTRICAL RESISTANCE IN ORGAN-ON-A-CHIP MICROSYSTEMS

CROSS-REFERENCE TO RELATED APPLICATIONS

This application is a national stage of International Application No. PCT/US2018/019754, filed on Feb. 26, 2019, which claims priority to and benefit of U.S. Provisional Patent Application No. 62/506,420, filed May 15, 2017, and U.S. Provisional Patent Application No. 62/464,229, filed Feb. 27, 2017, each of which is hereby incorporated by reference herein in its entirety.

GOVERNMENT SUPPORT

This invention was made with government support under W911NF-12-2-0036 awarded by the Department of Defense/DARPA. The government has certain rights in the invention.

FIELD OF THE INVENTION

The present invention relates generally to micro-engineered cell culture models and, more particularly, to system combining both transendothelial/transepithelial electric resistance (TEER) and a multi-electrodes array (MEA).

BACKGROUND OF THE INVENTION

Micro-engineered cell culture models (Organs-on-Chips) have demonstrated higher resemblance to human physiology and drug response compared to conventional tissue culture. Unlike conventional cell assays, Organs-on-Chips are highly compatible with the integration of sensors enabling real-time cell function studies. Accordingly, the Organs-on-Chips have emerged as a new tool to recapitulate human physiology and drug responses.

Utilizing recent advances in micro-engineering and microfluidics, these models can reconstruct a physiologically relevant microenvironment and allow precise spatiotemporal control of endogenous cellular cues as well as exogenous stimuli including pharmaceutical compounds. Unlike traditional in vitro cell models, Organs-on-Chips allow for vascular perfusion, which is a critical aspect for gaining improved resemblance of physiological functions and pharmacokinetic ("PK") modeling.

Moreover, as an additional advantage over conventional cell culture systems, Organs-on-Chips enable easy integration of sensors for real-time assessment. Integrated sensing elements can give both spatially and temporally resolved information on basal cell function and pharmacodynamic ("PD") drug responses. This includes direct electrical function, such as generated action potentials and cell layer barrier function, as well as quantitative measurements of secreted substances, such as signaling proteins and metabolites. However, integration of several complementing sensing elements to assess multiple cellular functions are still not frequently reported in Organs-on-Chips.

The direct measurement of electrical resistance over a tissue barrier, also referred to as transendothelial/transepithelial electric resistance ("TEER"), is a fast, label-free, and highly sensitive measurement of the barrier integrity and permeability. TEER measurements reflect the ionic conductance of the paracellular junctions of a cellular monolayer and is a valuable metric of all endothelial (vascular) and epithelial models.

TEER measurements in Organ-on-Chips have been widely applied, for example, to blood-brain-barrier (BBB) models, intestinal models, and alveolar models. Electric circuit modeling has revealed that TEER electrodes in Organ-on-Chips provide accurate values if the TEER electrodes are integrated close to the cellular monolayer. On the other hand, electric signals recorded using electrodes located in Organs-on-Chips inlets and outlets have resulted in erroneous estimates of the TEER values. Multiple measurements allows factoring-in the effect of uneven current densities across the cell layers and the elaboration of an efficient correction model to extract realistic TEER values.

Extracellular measurements of electric cell activity in the form of multi-electrodes arrays ("MEAs") is an invaluable tool for assessment of neural and muscle cell function. For cardiac in vitro models, assessment of firing frequency or contraction/beat rate, as well as field potential ("FP") and its duration ("FPD") can be directly related to human patient data as the QT interval. In microfluidic Organ-on-Chips, integration of MEAs have been demonstrated to record neural network activity as well as field potential and drug responses of a myocardium using a flow cell combined with a commercial multi-electrodes array ("MEA") where electrodes were organized in a 8×8 electrode array. This electrode configuration of a commercial MEA considerably limits the applications in microfluidic-based Organs-on-Chips where more elaborated microchannel designs might be required.

Although TEER and MEA integration in Organs-on-Chips models have separately been shown to monitor critical pharmacodynamically relevant cellular functions, a shortcoming of present approaches is that there is no integration of the two sensing elements in a single Organ-on-Chip system.

The present disclosure is directed to providing a TEER-MEA system that solves the above and other needs.

SUMMARY OF THE INVENTION

According to one aspect of the present invention, an organ-on-chip device is directed to monitoring a biological function. The device has a body with a top microchannel and a bottom microchannel, and a membrane layer located at an interface region between the top microchannel and the bottom microchannel. The membrane includes a first type of cells adhered to a side facing toward the top microchannel, the first type of cells forming a barrier between the top microchannel and the bottom microchannel. The device further has a top layer along a top surface of the top microchannel with a first plurality of transendothelial electrical resistance (TEER) measurement electrodes enabling direct monitoring of cell function and electrical activity of the first type of cells on the membrane. The device also has a multi-electrode array (MBA) layer along a bottom surface of the bottom microchannel with a second plurality of TEER measurement electrodes. The MEA layer includes a second type of cells adhered to a side facing toward the bottom microchannel, the second plurality of TEER measurement electrodes enabling direct monitoring of cell function and electrical activity of the second type of cells on the MEA layer.

According to another aspect of the present invention, a method is directed to monitoring cell function and electrical activity in an organ-on-chip device. The method includes providing a microfluidic device having a top microchannel and a bottom microchannel, a top layer along a top surface of the top microchannel having a first plurality of transendothelial electrical resistance (TEER) measurement electrodes, and a membrane layer located at an interface region between the top microchannel and the bottom microchannel. The membrane includes a first type of electrically-active cells. The microfluidic device further includes a multi-electrode array (MBA) layer along a bottom surface of the bottom microchannel and having a second plurality of TEER measurement electrodes, the MEA layer including a second type of electrically-active cells adhered to a side facing toward the bottom microchannel. The method further includes monitoring, via the first plurality of TEER measurement electrodes, electrical activity of the first type of electrically-active cells on the membrane layer and, via the second plurality of TEER measurement electrodes, electrical activity of the second type of electrically-active cells on the MEA layer.

According to yet another aspect of the present invention, a method is directed to monitoring electrical activity in an organ-on-chip device. The method includes providing a microfluidic device having a first layer with a first plurality of transendothelial electrical resistance (TEER) electrodes, a second layer in the form of a multi-electrode array (MEA) and with a second plurality of TEER measurement electrodes, and a membrane layer located at an interface region between the first layer and the second layer. The method further includes measuring at least one of an electrical value or a cell characteristic of at least one of (i) a first type of electrically-active cells adhered to the membrane layer, or (ii) a second type of electrically-active cells adhered to the second layer.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 1A is a top-view image of an MEA-TEER device.

FIG. 1B is a perspective exploded view illustration of the MEA-TEER device of FIG. 1A.

FIG. 1C is a schematic illustration of an experimental design using the MEA-TEER device of FIG. 1A.

FIG. 2A is a scanning electron microscope ("SEM") image of electrodes of a bottom layer of the MEA-TEER device of FIG. 1A.

FIG. 2B is an image showing MEAs of the MEA-TEER device of FIG. 1A being electroplated with Platinum black.

FIG. 2C is a graph illustrating cardiomyocytes measured from regular Platinum electrodes.

FIG. 2D is a graph illustrating cardiomyocytes measured from Platinum black electrodes.

FIG. 4A is an image of an endothelial monolayer of the MEA-TEER device of FIG. 1A, illustrating a non-treated control model.

FIG. 4B is an image of the endothelial monolayer of the MEA-TEER device of FIG. 1A, illustrating isoproterenol treatment of the model.

FIG. 4C is an image of the endothelial monolayer of the MEA-TEER device of FIG. 1A, illustrating TNF-α 2 and isoproterenol treatment of the model.

FIG. 4D is an image of a myocardium tissue in the MEA-TEER device of FIG. 1A, illustrating the non-treated control model.

FIG. 4E is an image of the myocardium tissue of the MEA-TEER device of FIG. 1A, illustrating isoproterenol treatment of the model.

FIG. 4F is an image of the myocardium tissue of the MEA-TEER device of FIG. 1A, illustrating TNF-α 2 and isoproterenol treatment of the model.

FIG. 4G is an image illustrating the MEA electrodes and the TEER electrodes of the MEA-TEER device of FIG. 1A.

FIG. 5A is a graph illustrating TEER impedance values over time for the MEA-TEER device of FIG. 1A.

FIG. 5B is a graph illustrating TEER capacitance values over time for the MEA-TEER device of FIG. 1A.

FIG. 5C is a graph illustrating beat rate of the measured values of FIGS. 5A and 5B, in response to addition of isoproterenol.

FIG. 5D is a graph illustrating corrected field potential duration ("cFPD") of the measured values of FIGS. 5A and 5B, in response to addition of isoproterenol.

FIG. 10A is an image of an endothelial monolayer of the MEA-TEER device of FIG. 6A, illustrating a non-treated control model.

FIG. 10B is an image of the endothelial monolayer of the MEA-TEER device of FIG. 6A, illustrating isoproterenol treatment of the model.

FIG. 10C is an image of the endothelial monolayer of the MEA-TEER device of FIG. 6A, illustrating TNF-α 2 and isoproterenol treatment of the model.

FIG. 10D is an image of a myocardium tissue in the MEA-TEER device of FIG. 6A, illustrating the non-treated control model.

FIG. 10E is an image of the myocardium tissue of the MEA-TEER device of FIG. 6A, illustrating isoproterenol treatment of the model.

FIG. 10F is an image of the myocardium tissue of the MEA-TEER device of FIG. 6A, illustrating TNF-α 2 and isoproterenol treatment of the model FIG. 10G is an image illustrating the MEA electrodes and the TEER electrodes of the MEA-TEER device of FIG. 6A.

Figure 2E:
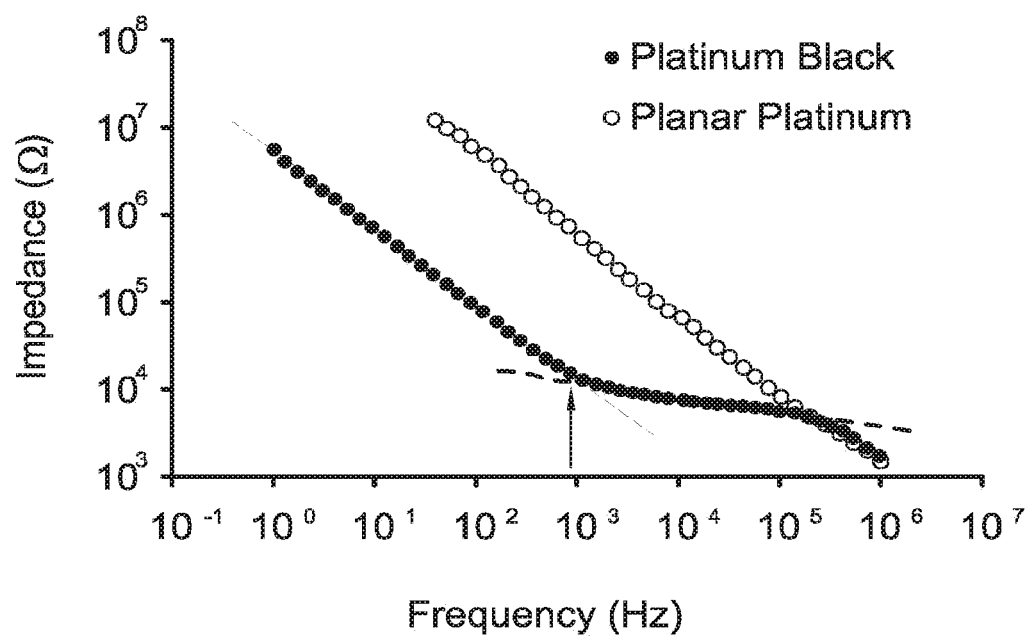
FIG. 2E is a graph illustrating impedance spectroscopy of the Platinum black electrodes in comparison to the regular Platinum electrodes.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation." Where a range of values is disclosed, the respective embodiments include each value between the upper and lower limits of the range.

The present disclosure is generally directed to a novel combination of MEAs with transendothelial electrical resistance TEER measurement electrodes into a single microfluidic Organ-on-Chip system. The electrode materials and the chip geometry are optimized for functional studies of a barrier-forming endothelial layer and a layer of electrically active cells.

Additionally, by way of specific application example, a vascularized heart tissue is engineered in this system. Human primary endothelial cells form a vascular barrier in one compartment interfacing a myocardium formed by cardiomyocytes derived from human induced pluripotent stem cells. Alteration of the barrier and cardiac function using the pro-inflammatory cytokine TNF-α and the drug isoproterenol demonstrate the sensitivity of the MEA-TEER device for assessment of biological, as well as pharmaceutical stimulus.

Thus, by way of example, the novel integration of the two sensing elements in one Organ-on-Chip system is applicable to create an endothelialized myocardium, such as a vascularized Heart-on-Chip. The system is optimized to allow the real time and simultaneous assessment of endothelial barrier function combined with electrical activity, which is applicable to a variety of electrically active cells. For example, an MEA-TEER device is used to study a vascular disease associated process or an endothelial barrier degradation following an inflammatory stimulus (e.g., by TNF-α), while also monitoring the cardiac effects at the same time. In another example, the MEA-TEER device is further used to study a cardiac tissue response mimicking the vascular systemic delivery of a commonly used treatment of bradycardia, isoproterenol.

Referring generally to FIGS. 1A-1C, an exemplary embodiment shows an organ-on-chip device (also referred to as a microfluidic device) in the form of an MEA-TEER device 100. Referring specifically to FIG. 1A, which has a scale bar of 2.0 centimeters ("cm"), the MEA-TEER device 100 has MEA connectors 102 (Platinum), TEER electrodes 104 (Gold), and a microfluidic chip 106 on top of MEA electrodes 108. In FIG. 1B, the MEA-TEER device 100 shows five layers of the device: an MEA platform 110, a first fluidic layer made of polydimethylsiloxane ("PDMS") 112, followed by a polyethylene terephthalate ("PET") membrane layer 114, a top chip microchannel 116, and a TEER layer 118.

According to one example, the MEA platform 110 is a custom Platinum microelectrode array on a glass layer, the PDMS layer 112 having a thickness of about 1 millimeter ("mm"), the top chip microchannel 116 has a PDMS substrate with a thickness of about 0.4 mm, and the TEER layer 118 has gold-patterned polycarbonate electrodes. In FIG. 1C, an endothelial layer 120 is grown on top of the PET membrane layer 114, while cardiomyocytes 122 are cultured on top of the MEA platform 110. Both cell types 120, 122 are cultured between the two sets of TEER electrodes on the MEA platform 110 and the TEER layer 118, A fluid typically flows through either or both of the top (or apical) microchannel 116 and a bottom (or basal) microchannel 117, which are part of a device body 119.

The membrane layer 114 is located at an interface region between the top microchannel 116 and the bottom microchannel 117. The TEER layer 118 is also generally referred to as a top layer that is along a top surface of the top microchannel 116 and has a first plurality of TEER measurement electrodes for enabling direct monitoring of cell function and electrical activity of endothelial cells of the endothelial layer 120, which are also referred to as cells of a first type. The MEA platform 110 is also generally referred to as an MEA layer positioned along a bottom surface of the bottom microchannel 117 and having a second plurality of TEER measurement electrodes for enabling direct monitoring of cell function and electrical activity of the cardiomyocytes 112, which are also referred to as cells of a second type.

Figure 2F:
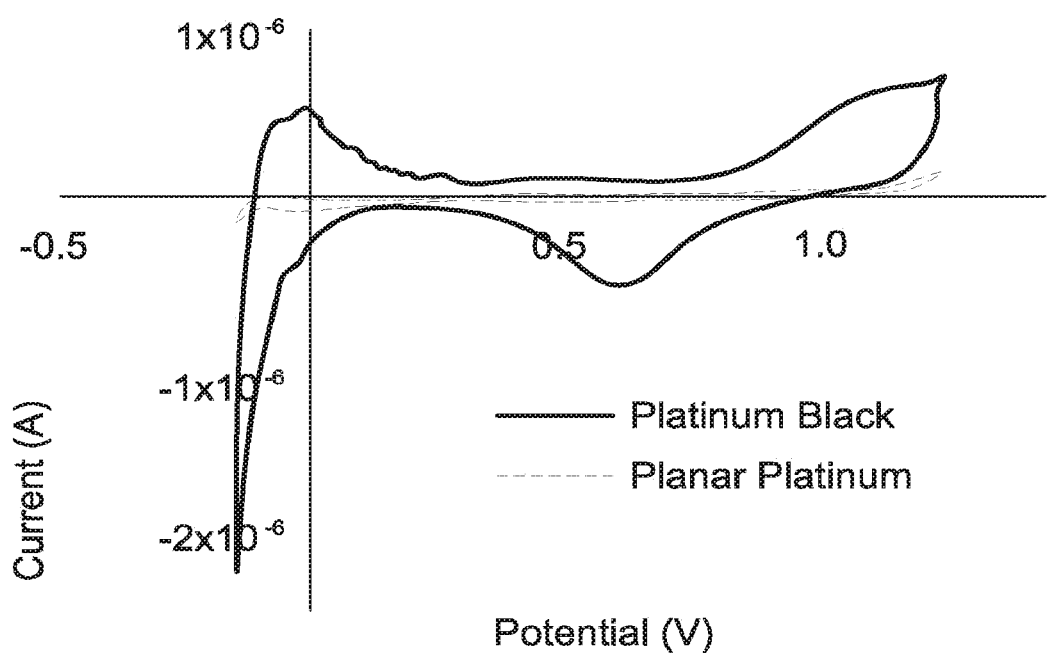
FIG. 2F is a cyclic voltamogram graph.

Referring to FIGS. 2A-2F, a general description is provided in reference to the MEA fabrication and characterization. In FIG. 2A, an SEM image illustrates a bottom layer of electrodes. Specifically, TEER electrodes 130 are on top and MEA electrodes 132 are on the bottom. In FIG. 2B, to increase the signal-to-noise ratio ("S/N"), the MEA electrodes 132 are electroplated with Platinum black, which increases the surface area. In FIGS. 2C and 2D, the FP of cardiomyocytes is measured from Platinum electrodes (FIG. 2C) and Platinum black electrodes (FIG. 2D). The signal has a four-time higher S/N, with less background effects. In FIG. 2E, an impedance spectroscopy graph shows that Platinum black electrodes decrease the impedance values three orders of magnitude in comparison to regular Platinum electrodes. In FIG. 2F, a cyclic voltammogram shows the graphs of regular Platinum and Platinum Black.

Figure 3A:
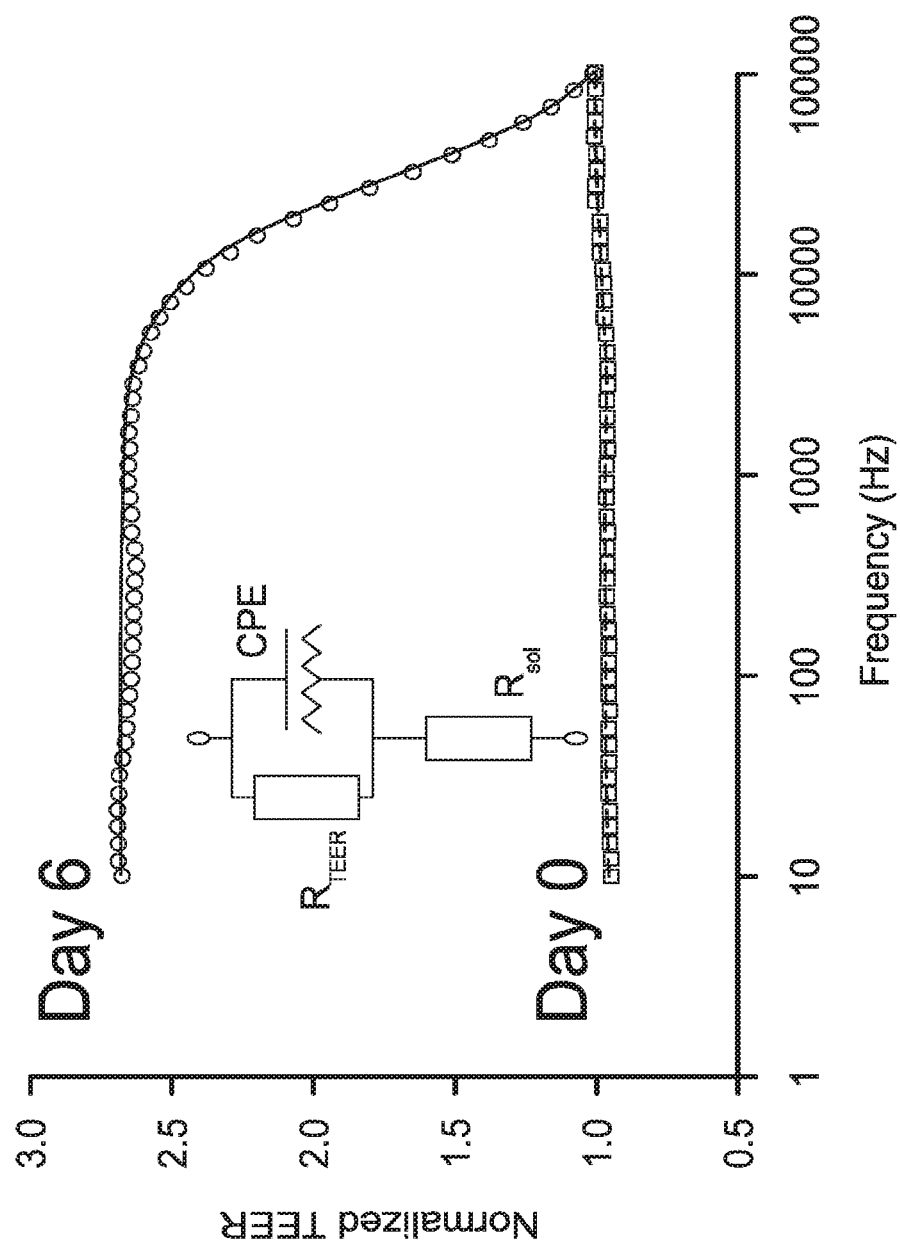
FIG. 3A is a graph illustrating a swipe impedance measurement of the MEA-TEER device of FIG. 1A.
Figure 3B:
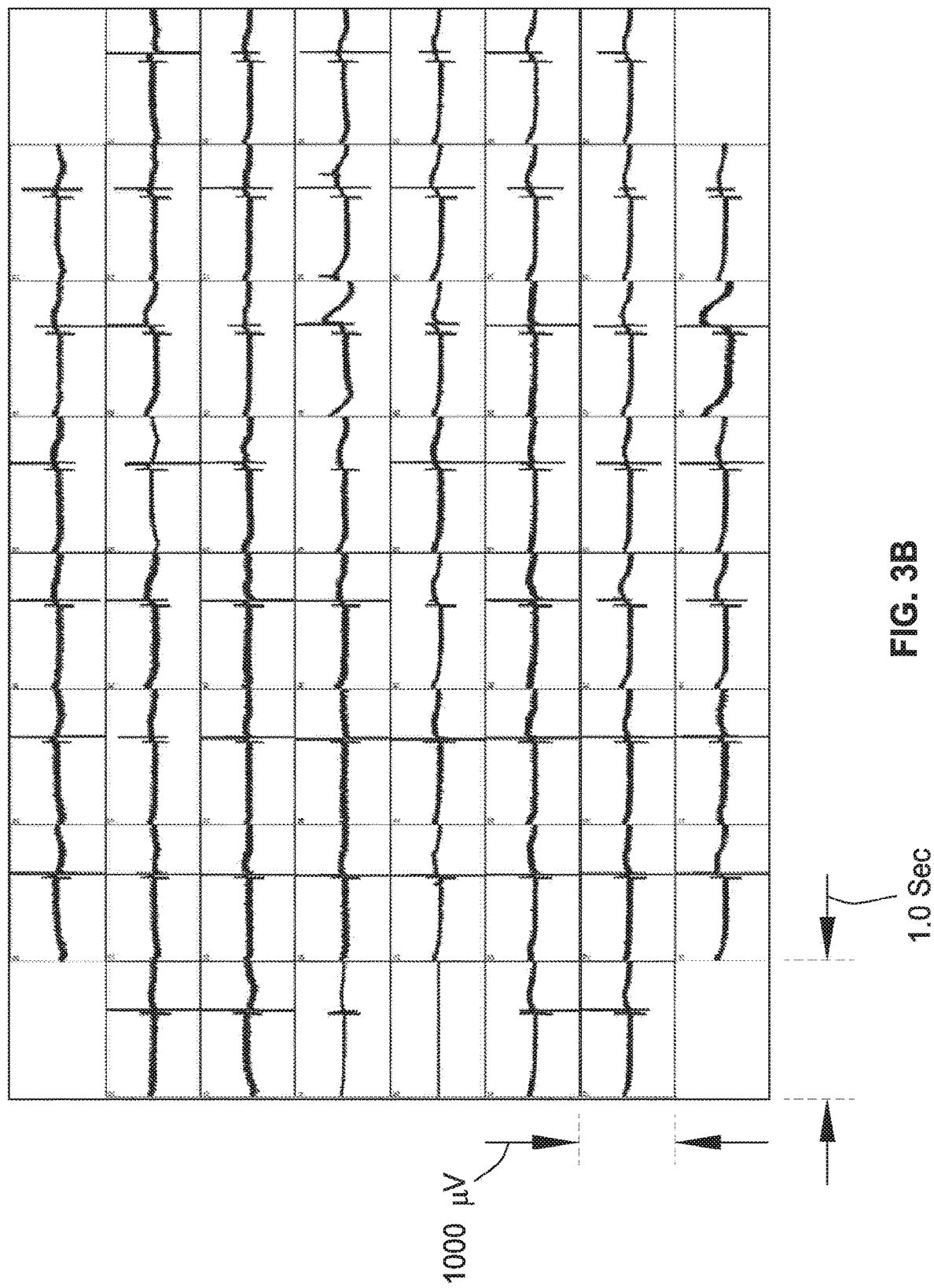
FIG. 3B is a plot illustrating a recording of a spontaneous beating.
Figure 3C:
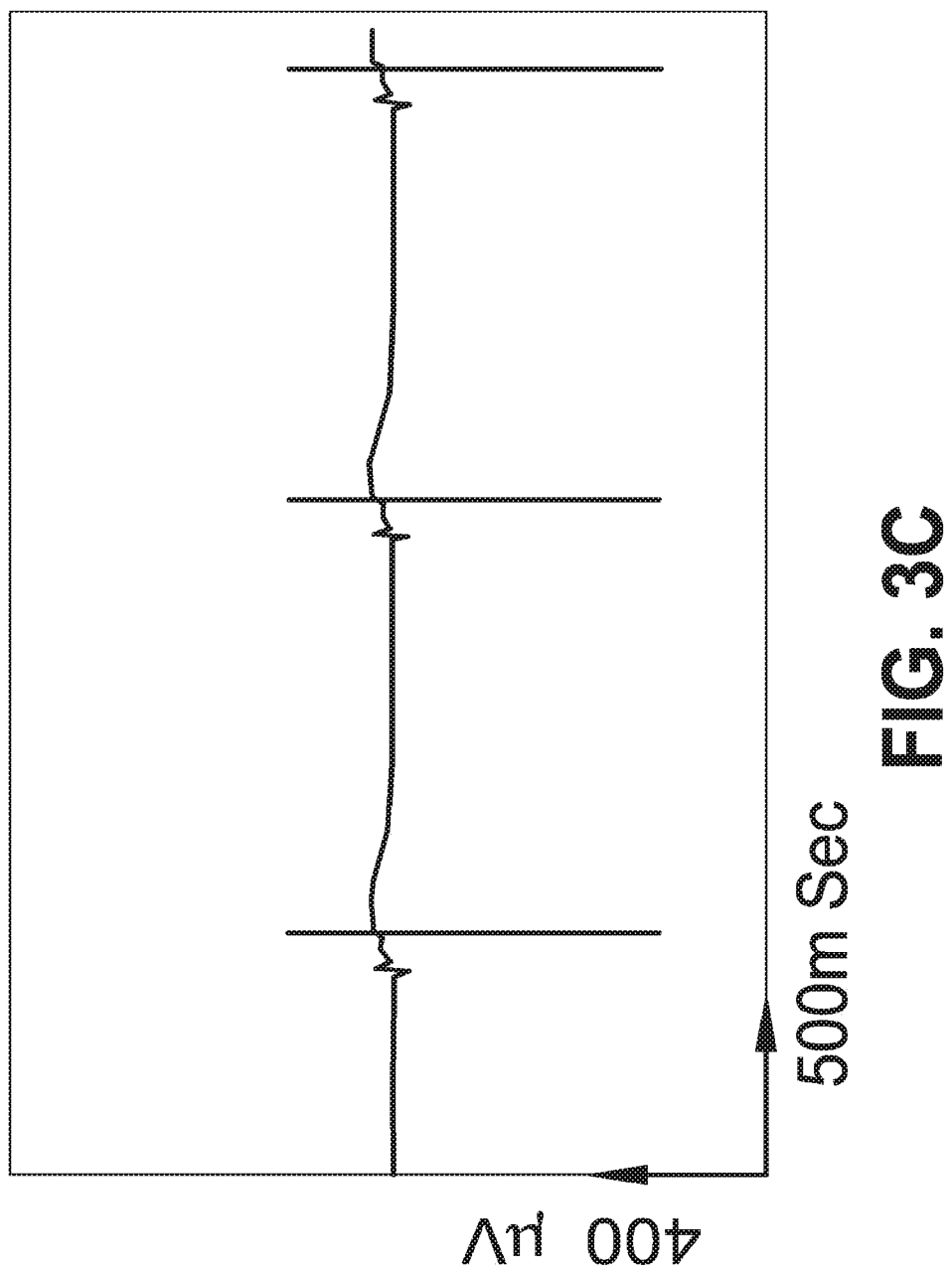
FIG. 3C is a plot illustrating a trace of a single electrode.

Referring to FIGS. 3A-3C, graph and plot illustrations show TEER and MEA measurements. In FIG. 3A, a swipe impedance measurement shows a graph with over 100 kilohertz ("KHz") frequencies (shown with a solid line) and data analysis (shown with a dashed line). In FIG. 3B, spontaneous beating is recorded by the MEA arrays showing that all the electrodes are functional. In FIG. 3C, a plot illustrates the MEA trace of a single electrode.

Referring to FIGS. 4A-4G, images illustrate the endothelial layer 120 and the cardiomyocytes 122 of a myocardium tissue in the MEA-TEER device 100 illustrated in FIGS. 1A-1C. In FIGS. 4A-4C, immunocytochemistry ("ICC") of the confluent endothelial layer 120, V-Cadherin, was used to stain adherens cellular junctions, with FIG. 4A illustrating non-treated control that reveals a confluent endothelial layer. FIG. 4B illustrates isoproterenol treatment that does not show any change in integrity of a barrier (as supported by the TEER data). In FIG. 4C, using TNF-α 0.2 caused damage to the barrier, with holes observed to decrease in the TEER values. The scale bar is 10 micrometers ("μm").

In FIGS. 4D-4F, images show immunohistochemistry ("IHC") of myocardial tissue on the MEA platform 110 (α-actinin), with FIG. 4D illustrating non-treated control and FIG. 4E illustrating isoproterenol treatment. The cardiomyocytes do not show major changes between the control samples and the drug addition. The scale bar here is also 10 μm. In FIG. 4F, an overview illustrates the myocardial tissue that is formed in the lower microchannel of the chip, i.e., the MEA platform or layer 110. Referring to FIG. 4G, an image shows the TEER electrodes 104 and the MEA electrodes 108. The scale bar of this image is 50.0 mm.

Referring to FIGS. 5A-5D, graphs illustrate drug manipulation in the MEA-TEER device 100. The TEER values of the endothelial layer 120 are measured and calculated as described above. In FIG. 5A, the TEER impedance values develop over time based on the endothelial cell proliferation and the formation of a confluent layer. TNF-α is added at day S and the TEER values decrease to the same values as ECM-coated chips without cells chip, while the control sample shows maintained TEER impedance values. In FIG. 5B, contrary to the TEER impedance values of FIG. 5A, TEER capacitance values demonstrate the opposite trend, with the TNF-α addition increasing the capacitance significantly. In FIG. 5C, the addition of isoproterenol shows an increase in the beat rate by 60%. In FIG. 5D, the addition of isoproterenol shows an increase in the cFPD by more than 20%.

Figure 6A:
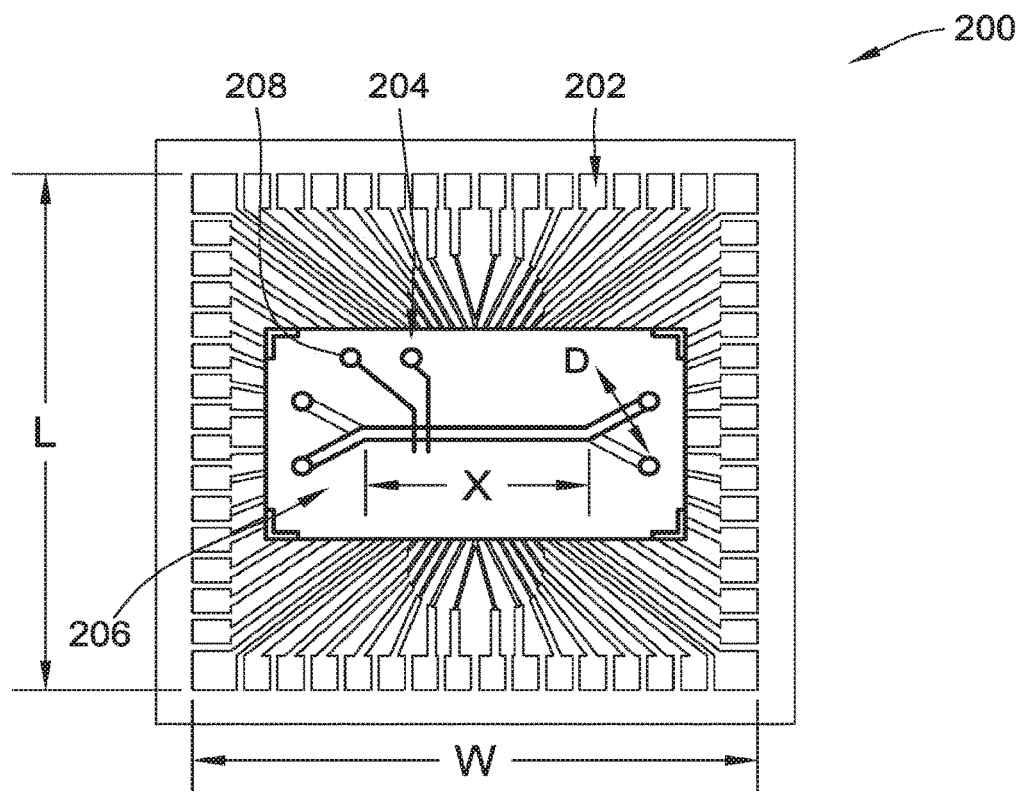
FIG. 6A is a top-view image of an MEA-TEER device, according to an alternative embodiment.
Figure 6B:
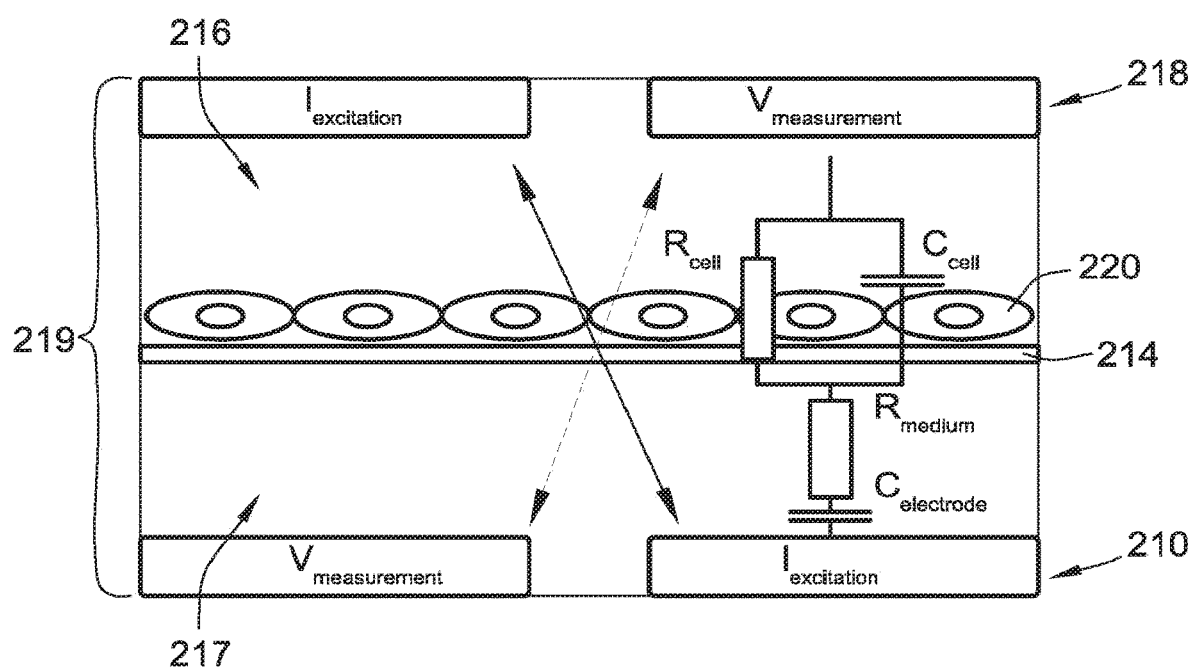
FIG. 6B is a schematic illustration of an experimental design using the MEA-TEER device of FIG. 6A.

Referring generally to FIGS. 6A and 6B, a further exemplary embodiment shows another MEA-TEER device 200 that is similar, but not necessarily identical, to the MEA-TEER device 100. For brevity, functions and features of one of the MEA-TEER devices 100, 200 are optionally included in the other one of the MEA-TEER devices 100, 200 even if not specifically described. Referring specifically to FIG. 6A, the MEA-TEER device 200 has MEA connectors 202, TEER electrodes 204, and a microfluidic chip 206 on top of MEA electrodes 208. The MEA-TEER device 200 has a generally square shape spanning about 49 mm across each of the length L and width W of the MEA array. The microfluidic chip 206 has an inner microchannel length X of about 15.5 mm and a microchannel width D of about 1.0 mm. In reference to FIG. 6B, an endothelial layer 220 is grown on top of a membrane layer 214. The cells of layer 220 are cultured between TEER electrodes on an MEA layer 210 and TEER electrodes on a TEER layer 218, Optionally, the MEA-TEER device 200 is similarly structured to the MEA-TEER device 100 of FIG. 1A, having similar or identical layers. A fluid typically flows through either or both of the top (or apical) microchannel 216 and a bottom (or basal) microchannel 217, which are part of a device body 219.

Figure 7B:
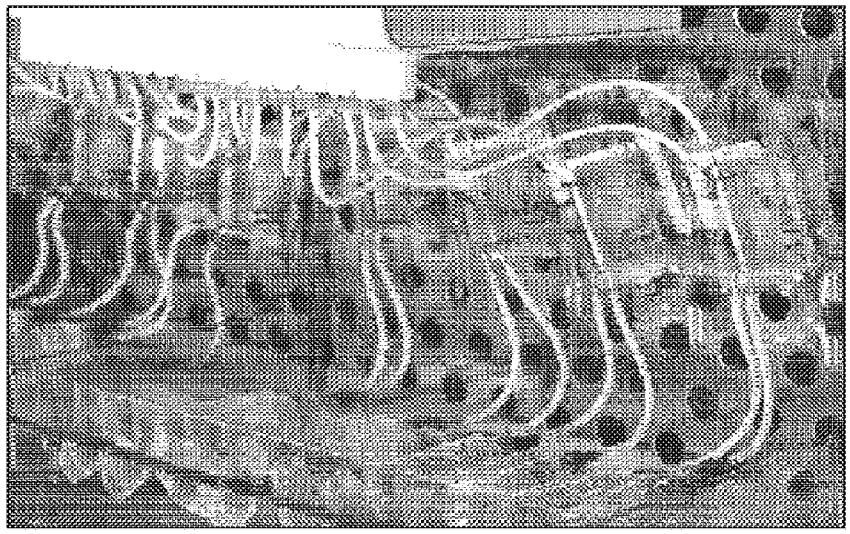
FIG. 7B is a perspective view illustration of the set-up of FIG. 7A.
Figure 7A:
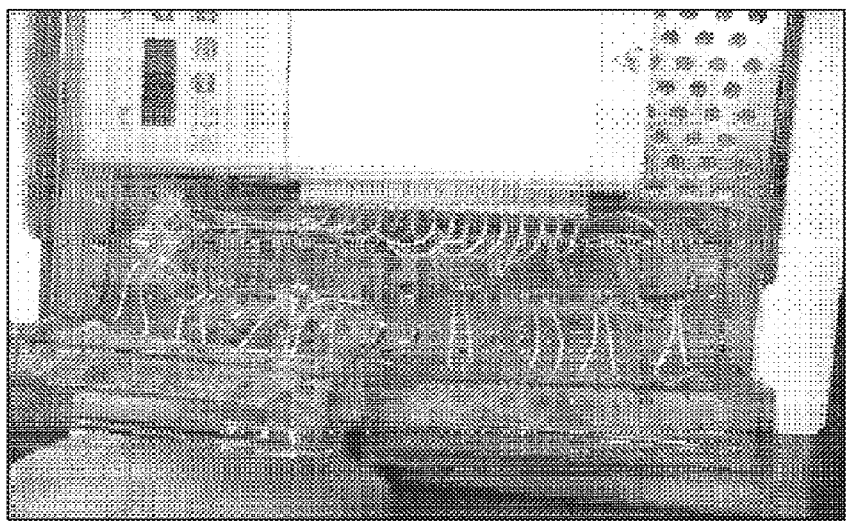
FIG. 7A is a top view illustration of a set-up with multiple MEA-TEER chip devices similar or identical to the MEA-TEER device of FIG. 6A.

Referring to FIGS. 7A and 7B, the MEA-TEER device 200 is included in an experimental model for making TEER and/or MEA measurements. In the illustrated example, multiple devices 200 (e.g., eight devices 200) are used for the measurements. For example, measurements are made to determine the shear stress when equal flow rates are in both channels 216, 217 of each device 200.

Figure 8A:
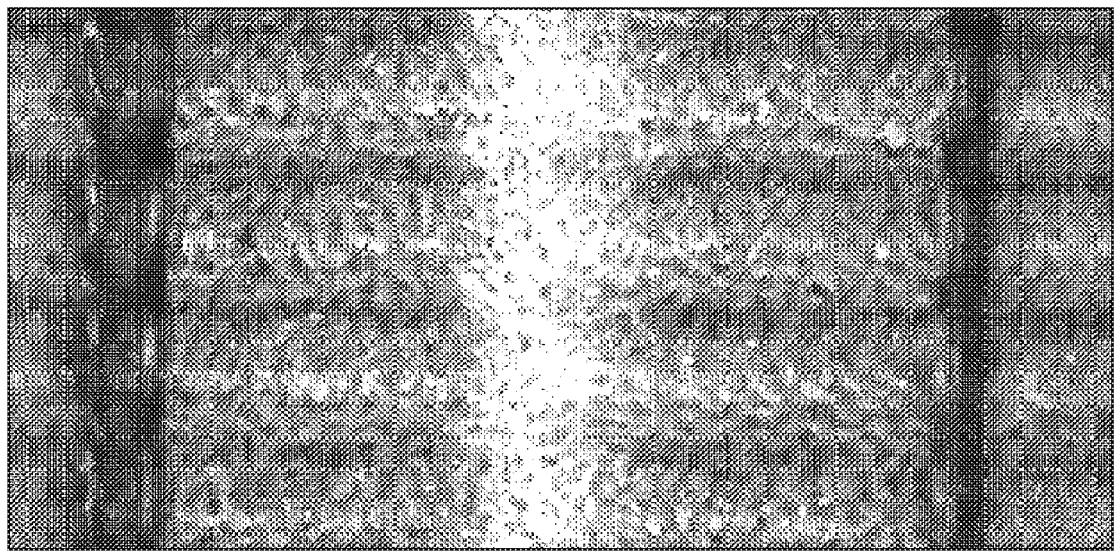
FIG. 8A is an image showing human umbilical cord vascular endothelial cells introduced in an apical microchannel of the MEA-TEER device of FIG. 6A.
Figure 8B:
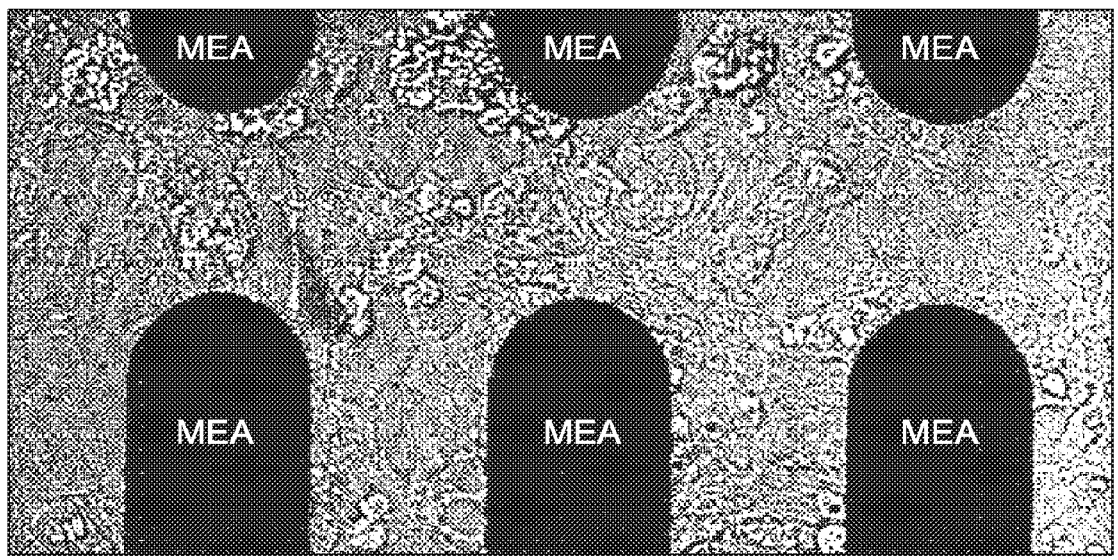
FIG. 8B is an image showing cardiomyocytes integrated into a basal microchannel of the MEA-TEER device of FIG. 6A.

Referring to FIGS. 8A and 8B, images show a monolayer and cardiomyocytes in the channels 216, 217 of the MEA-TEER device 200. Specifically, in FIG. 8A an apparent confluent monolayer is illustrated based on human umbilical vein endothelial cells ("HUVECs") introduced in the apical microchannel 216 of the MEA-TEER device 200. In FIG. 8B, an image shows cardiomyocytes that rapidly integrated into the basal microchannel 217 of the MEA-TEER device 200.

Figure 9B:
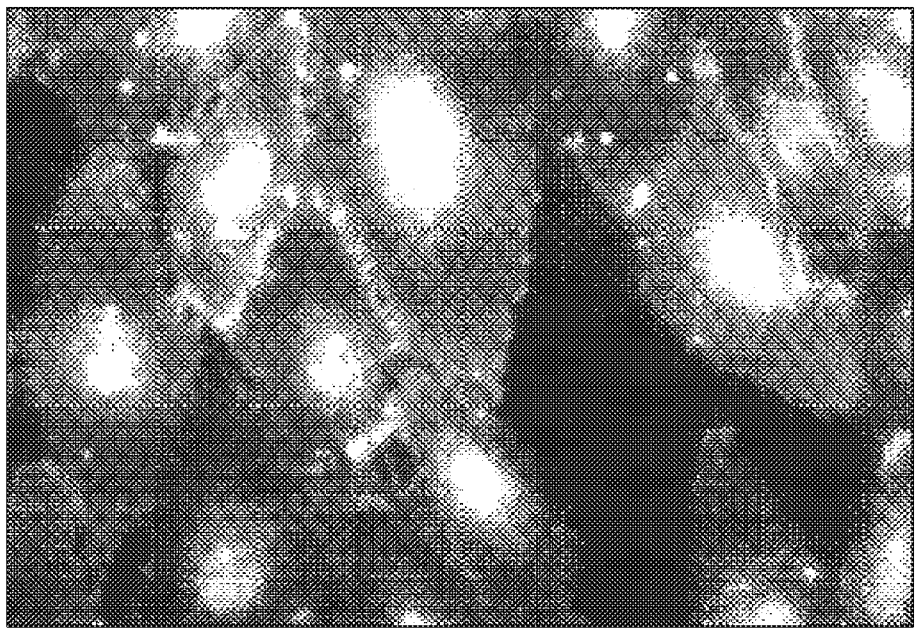
FIG. 9B is another image showing the severe damage to the barrier function in the MEA-TEER device of FIG. 6A.
Figure 9A:
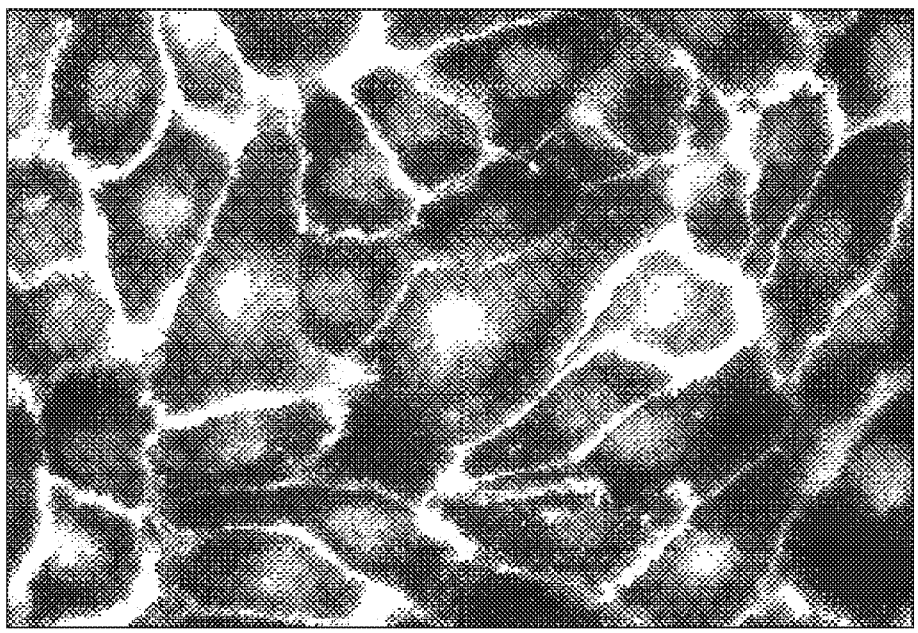
FIG. 9A is an image showing severe damage to a barrier function in the MEA-TEER device of FIG. 6A.

Referring to FIGS. 9A and 9B, images show damage to a barrier function. The damage is confirmed by changes in endothelial cytoskeleton, as well as visual micro gaps.

Referring to FIGS. 10A-10G, images show results suggesting that a TNF-α dose does not result in endothelial apoptosis. Specifically, images illustrate the endothelial layer 220 and cardiomyocytes of a myocardium tissue in the MEA-TEER device 200 illustrated in FIGS. 6A and 6B. In FIGS. 10A-10C, ICC of the confluent endothelial layer 220 is used to stain adherens cellular junctions, with FIG. 10A illustrating non-treated control that reveals a confluent endothelial layer. FIG. 10B illustrates isoproterenol treatment that does not show any change in integrity of a barrier (as supported by the TEER data). In FIG. 10C, using TNF-α 2 caused damage to the barrier, with holes observed to decrease in the TEER values. The scale bar is 10 μm.

In FIGS. 10D-10F, images show IHC of myocardial tissue on the MEA layer 210, with FIG. 10D illustrating non-treated control and FIG. 10E illustrating isoproterenol treatment. The scale bar here is also 10 μm. In FIG. 10F, an overview illustrates the myocardial tissue that is formed in the lower microchannel of the chip, i.e., the MEA layer 210. Referring to FIG. 10G, an image shows the TEER electrodes 204 and the MEA electrodes 208. The scale bar of this image is 50.0 mm.

Chip Fabrication—Microfluidic Layers.

Microfluidic channels are cut in 1 mm and 0.4 mm PDMS films that are prepared by spin coating Sylgard 1844 premixed in 1:10 ratio with a curing agent onto acrylic discs, and followed by curing at 80° C. for 30 minutes. Fluidic designs are plot-cut and protected from air contaminant during subsequent processing and storage by a PET film having a thickness of 100 μm. A disc bearing the PDMS channels is finally laser-cut into individual parts and stored under ambient conditions until further use.

Chip Fabrication—Electrode Patterning.

The MEAs are fabricated using standard microfabrication procedures. Borosilicate glass wafers (University Waters, USA) are sequentially coated with lift-off resist LOR20A (Microchem Corp USA, 3000 revolutions per minute ("rpm"), 60 seconds, soft-bake at 180° C. for 4 minutes) and imaging resist S1805 (Microchem Corp USA, 4000 rpm, 60 seconds, soft-bake at 115° C. for 1 minute). The MEA design, in one example, consists of 57 micro-band electrodes 100 μm wide, one reference electrode 200 μm wide and two 1400×500 μm rectangular electrodes for TEER measurement. All electrodes are designed to align along the length of the microfluidic microchannel.

The design is printed on transparency (Cad/art Services, USA), placed in hard-contact with the prepared wafer, and exposed to ultraviolet ("UV") light at 50 millijoules centimeter$^{-2}$ ("mJ·cm$^{-2}$") at 405 nanometers ("nm"). The exposed resin is developed (CD-21 developer, 75 seconds) and the wafers are thoroughly rinsed with deionized water, and then dried under a stream of nitrogen. Following an $O_2$ plasma descum, the prepared wafers are successively coated with titanium (10 nm) and platinum (90 nm) by e-beam evaporation (Denton, USA) before lifting-off the resin in Remover-PG (Microchem Corp USA, 60 minutes, 80° C.), rinsing with acetone and isopropanol, and drying under a stream of nitrogen.

Wafers are coated with 500 nm of silicon nitride ("$Si_3N_4$") by plasma-enhanced chemical vapor deposition ("PE-VCD"), coated with resin S1818 (Microchem Corp USA, 3000 rpm, 1 minute, soft-bake at 115° C. for 1 minute), and then contacts and electrode openings (MEA—30 μm in diameter separated by 200 μm; reference electrode—150× 350 μm; TEER electrodes—two 450×750 μm electrodes separated by 500 μm) are patterned as previously described. The ($Si_3N_4$) layer is finally etched by inductively coupled plasma reactive ion etching (SPP Process Technology Systems, USA), sonicated in acetone, rinsed in isopropanol, and blow-dried in a stream of nitrogen. Wafers are finally coated with a protective layer of S1818 before dicing and releasing individual MEAs.

Polycarbonate substrates (PC) with a thickness of 1 mm re cut to size with a respective protective backing, and inlets and outlets drilled as required. The protective backings re removed, and the polycarbonate substrates are rinsed with isopropanol, dried under a stream of compressed air, and activated in oxygen plasma for 2 minutes (Technics USA, 20 SCCM $O_2$, 300 mT). The electrode patterns are laser-cut in silicon-coated paper backing and include two 1 mm-wide electrodes separated by 0.5 mm. The silicon-side of the resulting paper shadow-masks is gently applied on the activated polycarbonate substrates using a homemade-alignment jig. These substrates are sequentially coated with 3 nm of titanium and 25 nm of gold in a metal e-beam evaporator (Denton EE4). The paper shadow-masks re finally gently peeled off the polycarbonate substrates before chemical activation.

MEAs are exposed to pirahana solution (3:1. $H_2SO_4$conc: 30% $H_2O_2$) for 1 minute before being sonicated in deionized water for 10 minutes and dried under a stream of compressed air. Electrodeposition of Platinum Black is performed in a custom-made electroplating set-up including of all the required external connections and an open cell. All the microelectrodes are short circuited and electrochemically activated in 2 M $H_2SO_4$ by cyclic voltammetry in the potential range −0.2 Volts ("V") to +1.5V (100 scans, 1 V/sec). The MEAs are rinsed in deionized water and exposed to the Platinum Black plating solution (3.5% $H_2PtCl_6$ and 0.005% lead acetate in deionized water). The Platinum Black solution is prepared fresh and sonicated for 10 minutes before use, and is electro-deposited on all the electrodes in a single step by applying 5 consecutive −0.1V 60 seconds pulses. The MEAs are finally successively sonicated for 5 minutes in water and in acetone to remove any weakly bound Platinum Black solution. The resulting electrodes are characterized electrochemically and by field emission SEM (Zeiss Ultra55, USA).

Chip Fabrication—Device Assembly.

Before derivatization, the MEAs are cleaned in acetone, sonicated in isopropanol and blow dried in a strewn of nitrogen. The cleaned MEAs, PC substrates, and PDMS layers are activated in an oxygen plasma (Technics USA, 20 SCCM $O_2$, 300 mT) before being immersed for 20 minutes in a 1% aqueous solution of APTES (Sigma, for the MEAs and the PC substrates) and a 1% aqueous solution of GLYMO (Sigma, for the PDMS layers). The MEAs, PC substrates, and PDMS layers are rinsed in water and dried under a stream of compressed air.

The MEAs/PDMS layers and the PC substrates/PDMS layers are aligned and brought into contact, gently pressed together to ensure conformational contact, and baked at 60° C. overnight. These assembled MEA/PDMS and PC/PDMS parts (Fluidics parts) are plasma-activated together with laser-cut PET membranes. Activated fluidic parts and PET membranes are immersed for 20 minutes in a 1% aqueous solution of GLYMO and a 5% aqueous solution of APTES respectively to introduce an epoxy group at the surface of the PDMS layers and amino groups at the surface of the PET membrane. The fluidic parts and the membranes are rinsed in water, dried in a stream of compressed air, aligned and brought into contact, gently pressed together to ensure conformational contact, and baked at 60° C. overnight.

Referring back to FIGS. 1A and 1B, the integrated TEER-MEA chip device 100 is fabricated with a combination of standard photolithographic metal patterning of electrodes, plot cutting and molding for flow channels. To ensure bonding between the PDMS microfluidic layer 112 to the silicon nitride or the polycarbonate/PET membrane layer 114, silane functionalization using amine (APTES) and epoxy (GLYMO) reactions is employed. Stable monolayers of APTES are readily self-assembled onto oxidized silicon nitride via coupling of the silane moieties and the interface layer of silicon oxynitride produced during the oxidation process.

Similarly, APTES is assembled onto PET and PC, although monolayers are not typically obtained. Assembly is demonstrated to occur via interaction of the APTES amino end-group and the carboxylate residues produced at the surface of oxidized PET and PC. Bonding between epoxy-modified PDMS and amino-modified substrates normally occurs at room temperature within 10-20 minutes. However, longer curing times at 60° C. are highly beneficial to obtain long-term stability. While bonding PDMS to PC or $Si_3N_4$ is straight forward, bonding PET to PDMS requires the PDMS layers to be extremely flat and homogeneous in thickness.

Referring back to FIGS. 1A-1C and 6A-6B, the microfluidic channels 116, 117, 216, 217 are designed to apply low shear stress on sensitive electrically active cells in the bottom microchannel 117, 217 (1 mm thick), and higher shear stress on the top microchannel 116, 216 (0.4 mm thick). Further referring back to FIGS. 1C, 7A, and 7B, applications demonstrate that when equal flow rates are in both channels 116, 117, 216, 217, the bottom microchannel 117, 217 has 6.25 times lower shear stress, with a flow rate of 60 μL/hour ("hr") resulting in $6.8 \times 10^{-4}$ dynes/$cm^2$ compared to $4.3 \times 10^{-3}$ dynes/$cm^2$.

Cell Culture—Human Cell Source and Culture.

HUVECs (Lonza) were expanded in EGM media (Lonza) and used at passages 2-6 in the chip experiments. Human induced pluripotent stem cell-derived cardiomyocytes hiPSC-CMs, Cor.4U, Axiogenesis) were handled according to the vendor's instructions and used a passage 1 after thawing. Briefly, cryopreserved cells were thawed on fibronectin-coated cell culture vessels in the presence of 5 milligrams ("mg")/milliliters ("mL") puromycin to select for MYH6-positive cells. Three hours after thawing, the puromycin containing media was gently refreshed to wash out remaining cryopreservant (DMSO). Twenty-four hours after seeding, cell culture media was refreshed without puromycin. The following day, the cardiomyocytes were replated into the chips using 0.5% trypsin.

Cell Culture—Chip Culture.

The MEA-TEER chips are surface-treated with an oxygen plasma (Atto, Diener electronic GmbH, Germany at $O_2$, 15 standard cubic centimeters per minute ("sccm"), 100 Watts, 30 seconds) to create hydrophilic, sterile, flow systems. Both apical and basal channels 116, 117, 216, 217 are coated overnight with human fibronectin (Sigma at 100 micrograms ("μg"/mL in PBS with $Mg^{2+}$ and $Ca^{2+}$ at 4° C.). HUVECs were seeded at $2*10^6$ cell per mL in the apical microchannel, and, then, left static overnight.

Cardiomyocytes are seeded at $2*10^6$ cell per mL in the basal microchannel, followed by 3 hours to overnight inculcation, before connecting both channels 116, 117, 216, 217 to flow at 60 microliters ("µL")/hr. Flow is controlled by a peristaltic pump (Ismatech) and connections re in Pharmed tubing (Cole-Parmer) having a 0.511 inner diameter. Upon formation of a complete endothelial monolayer, the FBS content in the endothelial media is decreased from 2 to 0.5% and the cardiac media is switched to a serum free composition (as shown in FIGS. 4A, 4D, and 4G). To challenge the endothelial barrier TNF (Sigma) is added at 2 µg/mL in the bottom microchannel 117, 217 during overnight flow. Isoproterenol (Sigma) 50 nanomolar ("nM") is added to the endothelial microchannel for 30 minutes followed by MEA measurement.

Device Characterization and Measurements—TEER Measurement

TEER measurements are carried out by applying a 10 microamperes ("µA") sinusoidal excitation signal in a four-electrode set-up in the frequency range 100 KHz-10 hertz ("Hz"). AC measurements are preferable for TEER measurements to avoid charging effects over the cell membranes and the electrodes. The four-electrode set-up, utilizing one opposing pair of electrodes for current excitation and another opposing pair of electrodes for voltage sensing, provides benefits of eliminating contact resistance associated with two electrode measurements.

TEER and capacitance values are derived using the equivalent circuit and model depicted in FIGS. 3A, 6A, and 6B. A resistor $R_{sol}$ describes the solution conductivity, while the electric response of the endothelial layer is modeled using a resistor ($R_{TEER}$) and a constant phase element ($CPE_t$) in parallel to extract TEER of the cell-cell junctions, as well as the contribution of cell membrane capacitance and, indirectly, the overall monolayer surface area.

The mathematical expression of a CPE impedance is:

$$Z_{CPE} = \frac{1}{Y_o(j\omega)^n} \quad \text{Equation 1}$$

The impedance of the CPE is expressed as a function of the admittance Y. and an exponent in equaling 1 or 0 for an ideal capacitor or an ideal resistor respectively of the whole system.

The capacitance of the cell layer $C_{cell}$ was calculated from $Z_{CPE}$, using Equation 2:

$$C_{cell} = \frac{(Y_o \times R_{TEER})^{\frac{1}{n}}}{R_{TEER}} \quad \text{Equation 2}$$

Device Characterization and Measurements—MEA Characterization.

The impedance of the plain Platinum and Platinum Black-modified microelectrodes is characterized using electrochemical impedance spectroscopy in the frequency range 1 megahertz ("MHz")-1 Hz using, for example, a PGStat 128N (Metrohm AG, The Netherlands) with single sine excitation signals of 5 millivolts ("mV") in amplitude applied at the open circuit potential against an Ag/AgCl$_{(sat\ KCl)}$ reference electrode. The surface area and the roughness factor of the microelectrodes is extracted from cyclic voltammograms recorded in the range −0.2 V to 1.25V versus Ag/AgCl$_{(KCl)}$ in 2M sulfuric acid at a scan rate of 1 V/second. Charges associated with hydrogen absorption are translated into an area using 208 microcoulomb ("µC") $cm^{-2}$ as the conversion factor. Roughness factors are calculated by dividing the calculated real electrochemical surface area by the electrode geometrical area ($7.1 \times 10^{-6}$ $cm^2$).

The impedance of the electrodes in the MEA directly affects the FP amplitude and the signal-to-noise ratio ("S/N") of the signal from electrical cells. Referring to FIGS. 2C and 2D, increasing the surface area of the recording microelectrodes considerably decreases their intrinsic impedance. Referring to FIGS. 2A and 2B, Platinum Black is deposited on the microelectrodes using electroplating. Because native Platinum Black coatings are notoriously fragile, the electrodes are consecutively sonicated, following plating, for 10 minutes in deionized water and isopropanol. This process removes all weakly-bound Platinum Black, with remaining Platinum Black being stable for cell culture.

As illustrated in FIG. 2F, the roughness factor is assessed by cyclic voltammetry in dilute sulfuric acid of the Platinum Black and is calculated to be 11.2±0.87. As seen with SEM, the resulting Platinum Black has outgrown the initial dimensions of the electrodes to a final diameter of 47.02±8.42 µm (n=10). For comparison, referring to FIGS. 2A-2C, the calculated roughness factor of a pristine Platinum electrode is 1.46±0.19. As further illustrated in FIG. 2E, in accordance with the inverse relation between the active electrode surface area and the impedance, the increased surface roughness decreases the microelectrode impedance >40 times at the cutoff frequency of 1151 Hz.

Device Characterization and Measurements—MEA Measurement.

Spontaneous cardiac field potentials ("FPs") are recorded from cardiomyocytes using Platinum and Platinum Black MEAs with the commercial Multi-Channel-System USB-MEA60-Inv-BC-System, Multi-Channel-Systems (MCS) GmbH. The micropatterned electrodes include ground electrodes. Cardiac FPs are recorded for 120 seconds for each measurement using Cardio2D software and are analyzed with Cardio2D+ (both from Multi Channel Systems). Measured parameters, including FP duration (FPD, milliseconds), peak-to-peak interval (PPI, seconds), beating rate (beats per minute), and conduction velocity (CV, centimers_1) are exported into Microsoft Excel files for further analysis. FPD is corrected using Fridericia's formula, cFPD=FPD/PPI$^{(1/3)}$, where cFPD is the rate-corrected FPD Device Characterization and Measurements—Immunocytochemistry.

Chips are rinsed in phosphate-buffered saline and fixated in 4% paraformaldehyde (Sigma) for 15 minutes at room temperature. ICC is carried out after permeabilization in phosphate-buffered saline with 0.05-0.1% Triton X-100 (Sigma) and blocking for 30 minutes in 3-5% Bovine Serum Albumin (Jackson ImmunoResearch, West Grove, Pa.) or 10% goat serum in phosphate-buffered saline with 0.05-0.1% Triton-X 100. Primary antibodies are applied in 2% goat serum or 0.5% BSA over-night at 4° C. or at RT The following primary antibodies are used for ICC experiments: mouse anti-vascular endothelial (VE)-cadherin (Abcam, 1:100), alpha-actinin (Abcam, 1:200) Cells are washed three times in phosphate-buffered saline with 0.05-0.1% Triton-X 100, followed by staining with secondary antibody staining for 30-60 min at RT. The secondary antibodies are anti-rabbit or anti-mouse IgG conjugated with Alexa Fluor-488, Alexa Fluor-555, or Alexa Fluor-647 (Invitrogen). Hoechst (10 mg/ml, Invitrogen) is used at a dilution of 1:5000 for nuclei staining, and Phalloidin-647 (invitrogen) is used for f-actin staining. Imaging is carried out in an Olympus confocal microscope (Olympus, Center Valley, Pa.) with appropriate filter cubes. Image processing is done using FIJI software.

MEA-TEER Heart-On-Chip Baseline Performance.

Referring to FIG. 8A, HUVECs are successfully introduced in the top microchannel 216 of the MEA-TEER device 200, and an apparent confluent monolayer is already observed after 24 hours. Similarly, referring to FIG. 8B, cardiomyocytes rapidly integrate into the bottom microchannel 217 of the MEA-TEER device 200, and a visual beating occurs within 24 hours. Thus, referring to FIGS. 3A-3C, 4A, and 10A-10G, the MEA-TEER device 200 illustrates the first demonstration of endothelialized myocardium models that allow a direct barrier and MEA measurements. Although vascularized heart models have been reported, which demonstrate the self-organization of endothelium and myocardium, these prior heart models lack direct electrical assessment of organ function. Similarly, although a densely endothelialized Heart-on-Chip model for drug evaluation has been previously reported, this prior model (unlike the MEA-TEER device 200 described above) relies on complex cell printing methods, as well as imaging strategies for determining the beat frequency.

Referring back to FIG. 3A the basal transendothelial resistance of the MEA-TEER device 100 is derived from the impedance spectroscopy and an equivalent circuit diagram. The applicability of this model is illustrated by the high model-data agreement (goodness-of-fit $\chi i^2$ 0.0087±0.013, i.e. <10% error). As further illustrated in FIG. 5A, four hours after cell seeding the transendothelial resistance is significantly higher than the background value. The TEER values continue to increase steadily and stabilize at day 2. The TEER values of the control chips average 232±47Ω for the following 4 days (n=12), demonstrating the stability of the endothelium over the course of the experiment. The stability of the endothelium is also reflected in the capacitance measurement, as illustrated in FIG. 5B. The culture membrane capacitance decreases after seeding and stabilizes at day 2 from 1190±194.63 nF before seeding to 226±89 nF during the rest of the experiment. On-chip capacitance measurements of the MEA-TEER device 100 are beneficial for following culture membrane coverage and cell adhesion, which reflects cell surface coverage.

Referring back to FIGS. 3B, 3C, SC, and SD, the first cardiac tissue function of the MEA-TEER device 100 is recorded 24 hours after the cardiomyocytes are seeded. Immediately, the Platinum black electroplating improvement is observed, as illustrated in FIGS. 2C and 2D, by a four-times higher S/N. The MEA measurement shows a basal average beat rate of 60 beats per minute and the basal rate-corrected field potential duration, the in vitro equivalent of the QT interval of 370-390 milliseconds. These values correlate to values previously reported for engineered Heart-on-Chip tissues without endothelium for the former or for the latter.

Impact of a TNF-α Challenge on the MEA-TEER Heart-On-Chip.

TNF-α is a pro-inflammatory cytokine mainly produced by stimulated macrophages and monocytes in systemic circulation. TNF-α has been shown to affect F-actin polymerization resulting in barrier degradation, clinically associated with both pulmonary endothelial and cerebral endothelial dysfunction. Using the disclosed MEA-TEER chip 100, a significant (p<0.01) barrier disruption of the endothelial monolayer is observed, as illustrated in FIG. 5A, with TEER values dropping from 230±±45Ω to 15±13Ω after 24 hours TNF-α (2 µg/mL). The decrease in TEER values is also accompanied by an increase in capacitance from 194±33 nF from stabilization after day 2 to 2968±52 nF after the TNF-α challenge, as illustrated in FIG. 58. This result is consistent with previous reports in which changes in cell capacitance were shown to correlate with morphological changes of cells, as illustrated in FIGS. 4A-4G, where increased values correlate to membrane folding and surface roughness.

Further referring to FIGS. 4C, 9A, 9B, and 10A-10G, the severe damage to the barrier function is further confirmed by changes in the endothelial cytoskeleton and visual micro gaps in the cellular junctions. Additionally, referring to FIGS. 10A-10G, increased prevalence of pyknotic nuclei is not observed in the monolayer, which suggests that the TNF-α dose does not result in endothelial apoptosis. TNF-α is also associated with cardiac disease and has been demonstrated to reduce contractility in hamster cardiomyocytes at 200 nanograms/ml[3].

Response to Isoproterenol of the MEA-TEER Heart-On-Chip. Isoproterenol is a non-selective $\beta_1$-adrenergic agonist and has been well characterized as treatment of bradycardia. Moreover, isoproterenol is a tool-box compound for characterizing physiological responses of in vitro heart models. When isoproterenol is applied in the basal microchannel 117 of the MEA-TEER device 100 at a concentration of 50 nM, the beat rate increases by 60%, as illustrated in FIG. 5C, while the cFPD increases by 25%, as illustrated in FIG. 5D. These results are comparable with previous reports of beat rate in a mono-channel fluidic system, where a concentration of 100 nM isoproterenol has changed the beat rate with 60%.

In addition to monitoring changes in cardiac layer by using the MEA features of the MEA-TEER devices 100, 200, TEER values measurements show that isoproterenol does not affect the endothelial barrier on the endothelial layer 120, as illustrated for example in FIGS. 5A and 5B. As expected, although the cardiomyocytes are highly affected by the isoproterenol, the endothelial barrier 120 is not affected by the drug, as illustrated in FIGS. 5A and 5B. Accordingly, this study demonstrates the advantage of the dual sensor systems, which can monitor both the barrier function and the electrical activity.

The disclosure above describes the first demonstration of a microfluidic device with an integrated MEA array and TEER on the same chip to enable the measurement of electrical activity, barrier function, and conformational changes. The MEA-TEER device 100, 200 allows simultaneous recording of drug effects and biological processes, demonstrated above with the pro-inflammatory TNF-α and the well-characterized $\beta_1$ adrenergic receptor agonist isoproterenol.

Moreover, a signal enhancing electroplating step is integrated in the multi-electrode fabrication, being especially suitable for future use of the MEA-TEER device 100, 200 with cells generating weaker electric signals. Additionally, the engineered MEA-TEER device 100, 200 demonstrates an advantageous concept for direct electrical assessment of an endothelialized myocardium. This new MEA-TEER device, 100, 200 paves the way for more complex real-time assessment of cardio-toxicity and vascular effects of novel drugs, for example, in the Heart-on-Chip MEA-TEER configuration, and also opens the door for systems assaying the blood-brain-barrier and neural tissue function.

Each of these embodiments and obvious variations thereof is contemplated as falling within the spirit and scope of the claimed invention, which is set forth in the following claims. Moreover, the present concepts expressly include any and all combinations and sub-combinations of the preceding elements and aspects.

What is claimed is:

1. A method comprising:
   a) providing a microfluidic device having
      i) a top microchannel and a bottom microchannel;
      ii) a top layer along a top surface of the top microchannel having a first electrode;
      iii) a membrane layer located at an interface region between the top microchannel and the bottom microchannel, the membrane layer having a first and second side; and
      iv) a bottom layer along a bottom surface of the bottom microchannel having a second electrode and a multi-electrode array (MEA); and
   b) seeding a first type of electrically active cells on the first side of the membrane layer and a second type of electrically-active cells on the second side of the membrane layer.

2. The method of claim 1, further comprising providing a cell culture media within the top and bottom microchannels.

3. The method of claim 1, wherein the first and second electrodes have transendothelial electrical resistance electrodes.

4. The method of claim 1, further comprising recording at least one signal using the first and second electrodes.

* * * * *